United States Patent
Fischer et al.

(10) Patent No.: US 6,455,472 B1
(45) Date of Patent: Sep. 24, 2002

(54) PHENYL-SUBSTITUTED CYCLIC ENAMINONES

(75) Inventors: Reiner Fischer, Monheim; Ralf Wischnat, Köln; Mark Wilhelm Drewes, Langenfeld; Markus Dollinger, Leverkusen; Christoph Erdelen, Leichlingen; Dieter Feucht, Monheim, all of (DE); Ingo Wetcholowsky, Vinhedo (BR); Ulrike Wachendorff-Neumann, Neuwied (DE); Ulrich Philipp, Köln (DE); Olga-Tatjana Rauch, Kronberg (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/831,261

(22) PCT Filed: Nov. 2, 1999

(86) PCT No.: PCT/EP99/08366

§ 371 (c)(1),
(2), (4) Date: Jul. 16, 2001

(87) PCT Pub. No.: WO00/27812

PCT Pub. Date: May 18, 2000

(30) Foreign Application Priority Data

Nov. 11, 1998 (DE) .......................................... 198 51 986

(51) Int. Cl.[7] ...................... C07D 207/08; A01N 43/26; A01N 43/32
(52) U.S. Cl. ...................... 504/138; 504/130; 540/610; 546/238; 548/566
(58) Field of Search ................................ 504/138, 130; 548/566; 546/238; 540/610

(56) References Cited

PUBLICATIONS

Glushkov, et al, 1990, Khim–Farm. Zh., (24)7, 24–7.*
Danhardt, et al, 1996, Pharmazie, 51(11), 805–810.*
Heteroccles, vol. 23, No. 10, (month unavailable) 1985, pp. 2645–2649, A. Corsaro, "A Convenient Synthesis of 2–Alkyl– and 2–Arylamino–4–Aryl–5–CyA Nothiazoles".
J. Indian Chem. Soc., vol. 48, No. 10, (month unavailable) 1971, pp. 953–956, H. K. Gakhar et al, "Thiopegan Derivatives. Part XLIX".
J. Org. Chem., 60, (month unavailable) 1995, pp. 2912–2915, I. Pendrak et al, "Synthesis and Anti–HSV Activity of Methylenedioxy Mappicine Ketone Analogs".
Pharmazie, 48, H. 6, (month unavailable) 1993, pp. 410–414, H. Lettau et al, "Synthese von Lipoxygenaseinhibitoren" 2.Mitteilung [1]: Synthese von Lactamarylhydrazonen und Tetrahydroazepinochinazolinon–arylhydrazonen.

Structural related to gyrase inhibitors: synthesis, cyclization and pharmacological activity.
J. Chem. Soc., (month unavailable) 1951, pp. 2758–2760, R. E. Bowman et al, "Experiments on the Synthesis of Carbonyl Compounds. Part V.* β–Keto–esters and –nitriles.".
C. R. Acad. Sci. Paris, t. 321, Série ll b, (month unavailable) 1995, p. 521–524, V. Issartel et al, "Réactions d'annélation stéréosélatives au départ d'une β–énaminone cyclique: l'α–pyrrolidinylidène–acétophénone".
Helvetica Chimica Acta, vol. 42, Fasc. 2, Nr. 69–70, (month unavailable) 1971, pp. 710–734, M. Roth et al, "70. Sulfidkontraktion via alkylative Kupplung: eine Methode zur Darstellung von βBicarbonylderivaten".
"Synthesis and Antibacterial Activity of 1,2–Polymethylene–4–Quinolone–3–Carboxylic Acids".
Pharm. Chem. J. (Engl. Trands), 25, (month unavailable) 1991, pp. 858–864, M. V. Mezentseva et al, "Synthesis and Antitumor activity of Pyrrolo[3,2–d]Pyrimidines".
J. Org. Chem., 55, (month unavailable) 1990, pp. 2246–2249, D. Brillon et al, "A New Preparation of Difunctionalized Enamines from Thioamides Using Silver(I) Carbonate".
J. Org. Chem., (46), (month unavailable) 1981, pp. 1221–1222, G. M. Coppola, et al, "Deuterium Isotope Effects in Carbon–13 Nuclear Magnetic Resonance Spectroscopy. Investigation of Tautomeric Equilibria in Enamino Ketone Systems".

* cited by examiner

Primary Examiner—Ceila Chang
Assistant Examiner—Andrea D. Small
(74) Attorney, Agent, or Firm—Joseph C. Gil; Raymond J. Harmuth

(57) ABSTRACT

The present invention relates to novel phenyl-substituted cyclic enaminones of the formula (I):

(I)

in which

Ar, X, Z, Y, K, n and m are each as defined in the description, to a plurality of processes and intermediates for their preparation and to their use as herbicides and pesticides.

11 Claims, No Drawings

PHENYL-SUBSTITUTED CYCLIC ENAMINONES

This application is a 35 U.S.C. 371 application of PCT application Ser. No. PCT/EP99/08366, filed on Nov. 2, 1999, which in turn claimed priority on German application 198 51 986.9, filed on Nov. 11, 1998.

FIELD OF THE INVENTION

The invention relates to novel phenyl-substituted cyclic enaminones, to a plurality of processes for their preparation, to intermediates and to the use of the enaminones as crop protection agents, in particular as herbicides, acaricides, nematicides and insecticides.

BACKGROUND OF THE INVENTION

Certain cyclic enaminones which are substituted in the phenyl ring have already been disclosed as intermediates for antibacterial quinolones (R. G. Glushkov, N. B. Marchenko, A. N. Padeiskaya, L. D. Shipilova, Pharmn. Chem. J. (Engl. Transl.) 24, 5460–465, (1990)). Furthermore, cyclic enaminones which are not substituted in the phenyl ring have been disclosed (M. V. Mezentseva, A. V. Kadushkin, L. M. Alekseeva, A. S. Sokolova, V. G. Granik, Pharm. Chem. J. (Engl. Transl.) 25, 858–864 (1991); G. M. Coppola, R. Damon, A. D. Kahle, M. J. Shapiro, J. Org. Chem. 46, 1221–1222, (1981); D. Brillon, G. Sauvé, J. Org. Chem. 55, 2246–2249, (1990)). A use of these compounds as crop protection agents has not yet been described.

SUMMARY OF THE INVENTION

Novel cyclic enaminones may be used as crop protection agents.

DETAILED DESCRIPTION

The novel cyclic enaminones are described in a general manner by the formula (I)

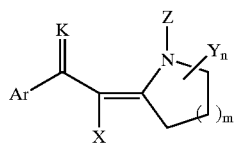

in which

K represents oxygen or sulphur,

Ar represents in each case substituted phenyl, naphthyl or represents in each case optionally substituted mono or bicyclic hetaryl having 5 to 10 ring atoms, X represents CN,

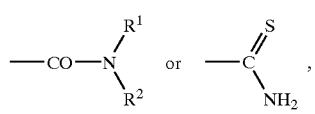

Y represents halogen or in each case optionally substituted alkyl, alkoxy, phenyl, phenylalkyl, hetaryl, hetarylalkyl or represents the groups

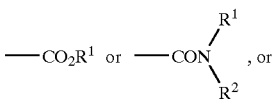

two adjacent $Y_n$ furthermore represent an optionally substituted saturated or unsaturated cycle which may optionally be interrupted by heteroatoms, and Z represents hydrogen, represents in each case optionally substituted alkyl, alkenyl, alkinyl, cycloalkyl, cycloalkyl-alkyl, alkoxyalkyl, phenoxyalkyl, phenylalkyl-oxyalkyl, phenylthioalkyl, phenylalkyl-thioalkyl, phenyl, phenylalkyl, hetaryl, hetarylalkyl or represents the groups

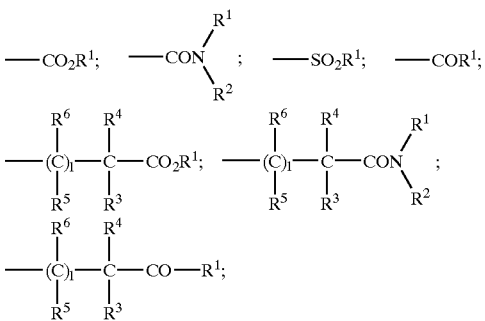

or cyano, l represents 0 to 3, m represents 1 to 3, n represents, depending on m, 0 to 4, $R^1$ represents hydrogen, represents in each case optionally substituted, saturated or unsaturated alkyl or cycloalkyl, each of which is optionally interrupted by heteroatoms, represents in each case optionally substituted phenyl or hetaryl, represents in each case optionally substituted phenylalkyl or hetarylalkyl, $R^2$ represents hydrogen, represents in each case optionally substituted, saturated or unsaturated alkyl or alkoxy, represents in each case optionally substituted phenyl, phenylalkyl or phenylalkyloxy, or $R^1$, $R^2$ together with the nitrogen atom to which they are attached may furthermore represent an optionally substituted cycle which is optionally interrupted by heteroatoms, $R^3$ represents hydrogen, represents in each case optionally substituted alkyl or alkoxy, represents in each case optionally substituted phenyl or phenylalkyl, $R^4$ represents hydrogen or represents optionally substituted alkyl, and $R^5$, $R^6$ independently of one another represent hydrogen or represent optionally substituted alkyl.

Compounds of the following formula:

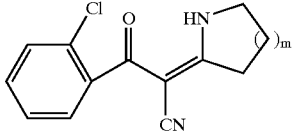

m = 1,2,3 are excluded.

For the compounds of the formula (I), the following applies:

Ar preferably represents $Ar^1$, where $Ar^1$ represents phenyl, naphthyl or mono- or bicyclic hetaryl having five to ten ring atoms, each of which radicals is optionally mono to pentasubstituted by halogen, $C_1$–$C_8$-alkyl, $C_2$–$C_8$-alkenyl, $C_2$–$C_8$-alkinyl, $C_1$–$C_8$-alkoxy, $C_2$–$C_8$-alkenyloxy, $C_3$–$C_8$-alkinyloxy, $C_1$–$C_8$-alkylthio, $C_1$–$C_6$-alkylsulphinyl, $C_1$–$C_6$-alkylsulphonyl, $C_1$–$C_6$-halogenoalkyl, $C_1$–$C_6$-halogenoalkoxy, $C_2$–$C_8$-halogenoalkenyloxy, $C_1$–$C_2$-alklidenediyi-dioxy, $C_1$–$C_2$-halogenoalkylidenediyl-dioxy, halogeno-$C_1$–$C_4$-alkylthio, halogeno-$C_1$–$C_4$-alkylsulphinyl, halogeno-$C_1$–$C_4$-alkylsulphonyl, hydroxyl, mercapto, nitro, cyano, amino, or by the groups

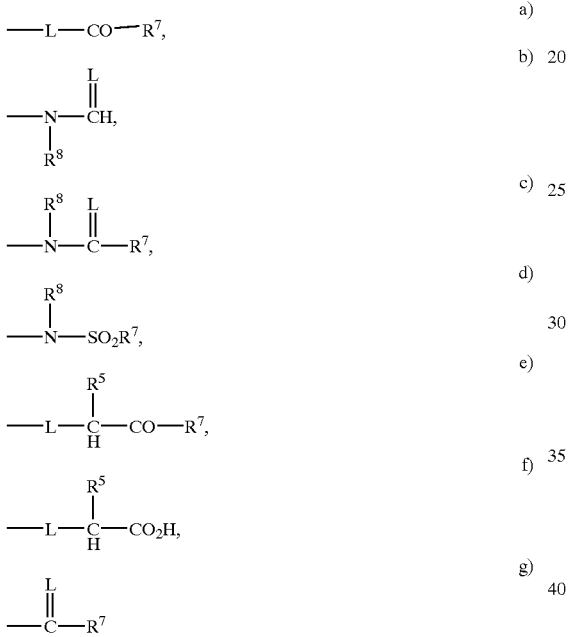

or represents $Ar^2$, where $Ar^2$ represents $Ar^1$ which is additionally substituted by phenyl, naphthyl, five- or six-membered hetaryl, phenyl-$C_1$–$C_4$-alkyl, phenoxy, phenyl-$S(O)_g$—, five- or six-membered hetaryloxy or hetaryl-$S(O)_g$, where these substituents for their part are in each case optionally mono- to tetrasubstituted by halogen, $C_1$–$C_6$-alkyl, $C_1$–$C_6$-alkoxy, $C_1$–$C_4$-halogenoalkyl, $C_1$–$C_4$-halogenoalkoxy, nitro or cyano.

K preferably represents oxygen or sulphur.

L preferably represents oxygen or sulphur.

X preferably represents CN,

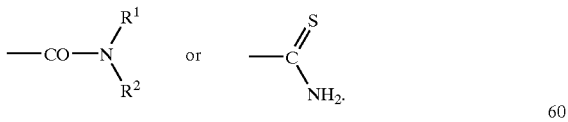

Y preferably represents halogen, $C_1$–$C_6$-alkyl, $C_1$–$C_4$-halogenoalkyl, $C_1$–$C_6$-alkoxy, represents phenyl, phenyl-$C_1$–$C_4$-alkyl, five- or six-membered hetaryl or five- or six-membered hetaryl-$C_1$–$C_4$-alkyl, each of which is optionally mono- to tetrasubstituted by halogen, $C_1$–$C_6$-alkyl, $C_1$–$C_6$-alkoxy, $C_1$–$C_4$-halogenoalkyl, $C_1$–$C_4$-halogenoalkoxy, cyano or nitro, or represents the groups

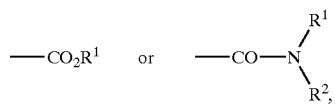

Two adjacent $Y_n$ preferably represent a 5- to 8-membered, saturated or unsaturated cycle which may be interrupted by 1 to 3 heteroatoms from the group consisting of N, O, S and which may optionally be mono- to trisubstituted by halogen, $C_1$–$C_4$-alkyl, $C_1$–$C_4$-alkoxy, $C_1$–$C_4$-halogenoalkyl, $C_1$–$C_4$-halogenoalkoxy, cyano or nitro.

Z preferably represents hydrogen, represents in each case optionally fluorine- and/or chlorine-substituted $C_1$–$C_8$-alkyl, cyano-$C_1$–$C_6$-alkyl, $C_3$–$C_8$-alknyl, $C_3$–$C_8$-alkinyl, $C_3$–$C_8$-cycloalkyl, $C_3$–$C_8$-cycloalkyl-$C_1$–$C_2$-alkyl, $C_1$–$C_4$-alkoxy-$C_1$–$C_4$-alkyl, $C_1$–$C_4$-halogenoalkoxy-$C_1$–$C_4$-alkyl, represents phenoxy-$C_1$–$C_4$-alkyl, phenyl-$C_1$–$C_4$-alkyloxy-$C_1$–$C_4$-alkyl, phenylthio-$C_1$–$C_4$-alkyl, phenyl-$C_1$–$C_4$-alkylthio-$C_1$–$C_4$-alkyl, phenyl, phenyl-$C_1$–$C_4$-alkyl, five- or six-membered hetaryl, five- or six-membered hetaryl-$C_1$–$C_4$-alkyl, each of which is optionally mono- to tetrasubstituted by halogen, $C_1$–$C_6$-alkyl, $C_1$–$C_6$-alkoxy, $C_1$–$C_4$-halogenoalkyl, $C_1$–$C_4$-halogenoalkoxy, nitro or cyano, or represents the groups

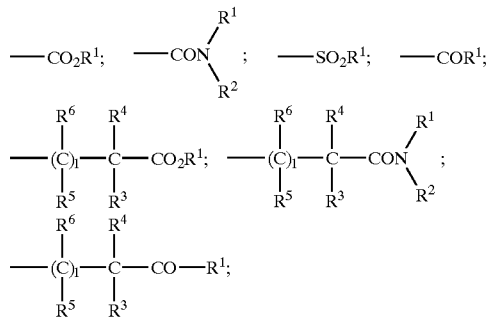

or cyano, where g preferably represents 0 to 2, l preferably represents 0 to 2, $R^1$ preferably represents hydrogen (but not for the radicals —$CO_2R^1$ and —$SO_2R^1$), represents in each case optionally fluorine- and/or chlorine-substituted $C_1$–$C_{10}$-alkyl, $C_2$–$C_{10}$-alkenyl, $C_3$–$C_6$-alkinyl, represents in each case optionally fluorine-, chlorine, $C_1$–$C_4$-alkyl, $C_1$–$C_4$-alkoxy-substituted $C_3$–$C_8$-cycloalkyl or $C_5$–$C_8$-cycloalkenyl in which optionally one methylene group may be interrupted by oxygen or sulphur, or represents phenyl, pyridyl, thienyl, pyrimidyl, thiazolyl, phenyl-$C_1$–$C_4$-alkyl, pyridyl-$C_1$–$C_2$-alkyl, thiazolyl-$C_1$–$C_2$-alkyl, each of which is optionally mono- to tetrasubstituted by halogen, $C_1$–$C_6$-alkyl, $C_1$–$C_6$-alkoxy, $C_1$–$C_4$-halogenoalkyl, $C_1$–$C_4$-halogenoalkoxy, cyano or nitro, $R^2$ preferably represents hydrogen, represents in each case optionally fluorine- and/or chlorine-substituted $C_1$–$C_6$-alkyl, $C_3$–$C_6$-alkenyl, $C_3$–$C_6$-alkinyl, $C_1$–$C_6$-alkoxy, $C_3$–$C_6$-alkenyloxy or represents phenyl, phenyl-$C_1$–$C_4$-alkyl or phenyl-$C_1$–$C_4$-alkoxy, each of which is optionally mono- to tetrasubstituted by halogen, $C_1$–$C_6$-alkyl, $C_1$–$C_6$-alkoxy, $C_1$–$C_4$-halogenoalkyl, $C_1$–$C_4$-halogenoalkoxy, cyano or nitro, $R^1$,$R^2$ together with the nitrogen atom to which they are attached furthermore preferably represent an in each case optionally $C_1$–$C_4$-alkyl-substituted five to eight-membered cycle in which optionally one methylene group may be replaced by oxygen or sulphur, $R^3$ preferably represents hydrogen, optionally halogen-substituted $C_1$–$C_6$-alkyl or represents phenyl or phenyl-$C_1$–$C_2$-alkyl each of which is optionally mono- to tetrasubstituted by halogen, $C_1$–$C_6$-alkyl, $C_1$–$C_6$-alkoxy, $C_1$–$C_4$-halogenoalkyl, $C_1$–$C_4$-halogenoalkoxy, cyano or nitro, $R^4$ preferably represents hydrogen or $C_1$–$C_6$-alkyl, $R^5$, $R^6$ independently of one another each preferably represent hydrogen or optionally fluorine- and/or chlorine-substituted $C_1$–$C_4$-alkyl, $R^7$ preferably represents in each case optionally fluorine- and/or chlorine substituted $C_1$–$C_{10}$-alkyl, $C_2$–$C_{10}$-alkenyl, $C_3$–$C_{10}$-alkinyl, $C_1$–$C_{10}$-alkoxy, $C_1$–$C_4$-alkoxy-$C_1$–$C_4$-alkyl, $C_1$–$C_4$-alkylthio-$C_1$–$C_4$-alkyl, in each case optionally fluorine- and/or chlorine-, $C_1$–$C_4$-alkyl, $C_1$–$C_4$-alkoxy-substituted $C_3$–$C_8$-cycloalkyl or $C_3$–$C_8$-cycloalkyloxy in which optionally one methylene group may be replaced by oxygen or sulphur, represents phenyl, phenoxy, benzyloxy, five- or six-membered hetaryl or phenyl-$C_1$–$C_4$-alkyl, each of which is optionally mono- to tetrasubstituted by halogen, $C_1$–$C_6$-alkyl, $C_1$–$C_6$-alkoxy, $C_1$–$C_4$-halogenoalkyl, $C_1$–$C_4$-halogenoalkoxy, cyano or nitro, or, in the case of the radicals a) and c) mentioned under Ar, also represents a group

or, for the radical g), also represents hydroxyl, $R^8$ preferably represents hydrogen or $C_1$–$C_4$-alkyl, $R^9$ preferably represents hydrogen, in each case optionally fluorine- and/or chlorine-substituted $C_1$–$C_{10}$-alkyl, $C_3$–$C_8$-alkenyl, $C_3$–$C_8$-alkinyl, $C_1$–$C_{10}$-alkoxy, $C_3$–$C_8$-alkenyloxy, optionally fluorine, chlorine, $C_1$–$C_4$-alkyl or $C_1$–$C_4$-alkoxy-substituted $C_3$–$C_8$-cycloalkyl in which optionally one methylene group may be replaced by oxygen or sulphur, represents phenyl, phenyl-$C_1$–$C_4$-alkyl or phenyl-$C_1$–$C_2$-alkoxy, each of which is optionally mono- to tetrasubstituted by halogen, $C_1$–$C_6$-alkyl, $C_1$–$C_6$-alkoxy, $C_1$–$C_4$-halogenoalkyl, $C_1$–$C_4$-halogenoalkoxy, cyano or nitro, $R^{10}$ preferably represents hydrogen, $C_1$–$C_6$-alkyl or $C_3$–$C_6$-alkenyl, $R^9$, $R^{10}$ together with the nitrogen atom to which they are attached preferably furthermore represent an optionally $C_1$–$C_4$-alkyl-substituted five- to eight-membered cycle in which optionally one methylene group may be replaced by oxygen or sulphur.

m preferably represents 1 to 3, n depending on m, preferably represents 0 to 3,

K particularly preferably represents oxygen or sulphur.

Ar particularly preferably represents $Ar^1$, where $Ar^1$ represents phenyl, naphthyl, quinolinyl, thienyl, pyrimidyl, furanyl, thiazolyl, benzothiazolyl, oxazolyl, pyrazolyl or pyridyl, each of which is optionally mono- to tri-substituted by fluorine, chlorine, bromine, $C_1$–$C_6$-alkyl, $C_2$–$C_6$-alkenyl, $C_2$–$C_6$-alkinyl, $C_1$–$C_6$-alkoxy, $C_3$–$C_6$-alkenyloxy, $C_3$–$C_6$-alkinyloxy, $C_1$–$C_6$-alkylthio, $C_1$–$C_4$-alkylsulphinyl, $C_1$–$C_4$-alkylsulphonyl, $C_1$–$C_4$-halogenoalkyl, $C_1$–$C_4$-halogenoalkoxy, $C_2$–$C_4$-halogenoalkenyloxy, $C_1$–$C_2$-alklidenediyi-dioxy, $C_1$–$C_2$-halogenoalkylidenediyl-dioxy, halogeno-$C_1$–$C_2$-alkylthio, halogeno-$C_1$–$C_2$-alkylsulphinyl, halogeno-$C_1$–$C_2$-alkylsulphonyl, hydroxyl, mercapto, nitro, cyano, amino or by one of the following groups

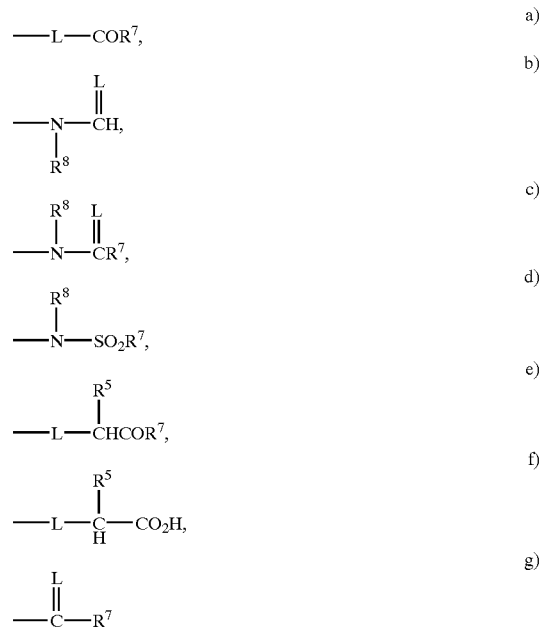

or represents $Ar^2$, where $Ar^2$ represents $Ar^1$ which is additionally substituted by phenyl, pyridyl, pyrimidyl, thienyl, furanyl, thiazolyl, tetrazolyl, triazolyl, benzyl, phenoxy, phenyl-$S(O)_g$—, pyridyloxy, pyrimidyloxy, thiazolyloxy, pyridyl-$S(O)_g$—, pyrimidyl-$S(O)_g$— or thiazolyl-$S(O)_g$—, where these substituents for their part are optionally mono- to tri-substituted by fluorine, chlorine, bromine, $C_1$–$C_4$-alkyl, $C_2$–$C_4$-alkenyl, $C_1$–$C_4$-alkoxy, $C_1$–$C_2$-halogenoalkyl, $C_1$–$C_2$-halogenoalkoxy, nitro or cyano, where g represents 0 to 2, L particularly preferably represents oxygen or sulphur.

X particularly preferably represents CN,

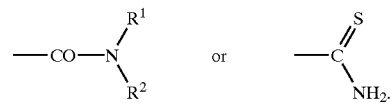

Y particularly preferably represents fluorine, $C_1$–$C_4$-alkyl, $C_1$–$C_2$-halogenoalkyl, $C_1$–$C_4$-alkoxy, represents phenyl, phenyl-$C_1$–$C_2$-alkyl, thiazolylmethyl, pyridylmethyl, each of which is optionally mono- to tri-substituted by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, cyano or nitro, or represents the groups

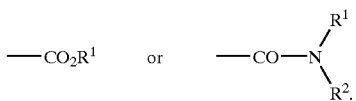

Two adjacent $Y_n$ may furthermore particularly preferably represent a 5- to 6-membered, saturated or unsaturated cycle which may be interrupted by a heteroatom from the group consisting of N, O, S and which may optionally be mono- to disubstituted by fluorine, chlorine, bromine, methyl, t-butyl, methoxy, trifluoromethyl, trifluoromethoxy, cyano or nitro.

Z particularly preferably represents hydrogen, represents in each case optionally fluorine- and/or chlorine-substituted $C_1$–$C_6$-alkyl, cyano-$C_1$–$C_3$-alkyl, $C_3$–$C_6$-alkenyl, $C_3$–$C_8$-alkinyl, $C_3$–$C_6$-cycloalkyl, $C_3$–$C_6$-cycloalkyl-$C_1$–$C_2$-alkyl, $C_1$–$C_4$-alkoxy-$C_1$–$C_2$-alkyl, $C_1$–$C_4$-halogeno-$C_1$–$C_2$-alkyl, represents phenoxy-$C_1$–$C_2$-alkyl, phenyl-$C_1$–$C_2$-alkyloxy-$C_1$–$C_2$-alkyl, phenylthio-$C_1$–$C_2$-alkyl, phenyl-$C_1$–$C_2$-alkylthio-$C_1$–$C_2$-alkyl, phenyl-$C_1$–$C_2$-alkyl, phenyl, pyridyl-$C_1$–$C_2$-alkyl, thiazolyl-$C_1$–$C_2$-alkyl, each of which is optionally mono- to tri-substituted by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, nitro or cyano, or represents the groups

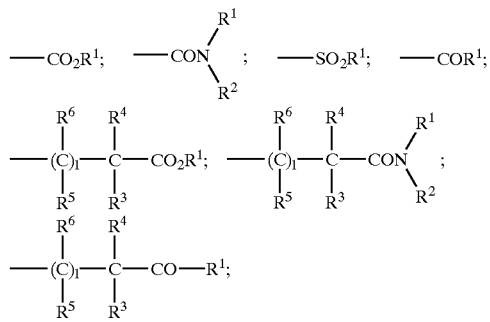

or cyano, where l particularly preferably represents 0 to 1, $R^1$ particularly preferably represents hydrogen (but not for the radicals —$CO_2R^1$ and —$SO_2R^1$), represents in each case optionally fluorine- and/or chlorine-substituted $C_1$–$C_6$-alkyl, $C_2$–$C_6$-alkenyl, $C_3$–$C_4$-alkinyl, represents optionally fluorine-, chlorine-, $C_1$–$C_2$-alkyl, $C_1$–$C_2$-alkoxy-substituted $C_3$–$C_6$-cycloalkyl or represents phenyl or benzyl, each of which is optionally mono- to disubstituted by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, cyano or nitro, $R^2$ particularly preferably represents hydrogen, represents in each case optionally fluorine- and/or chlorine-substituted $C_1$–$C_4$-alkyl, $C_3$–$C_4$-alkenyl, $C_3$–$C_4$-alkinyl, $C_1$–$C_4$-alkoxy, $C_3$–$C_4$-alkenyloxy or represents phenyl, benzyl or benzyloxy, each of which is optionally mono- to disubstituted by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, cyano or nitro, or $R^1$,$R^2$ together with the nitrogen atom to which they are attached particularly preferably furthermore represent an optionally $C_1$–$C_2$-alkyl-substituted five- or six-membered cycle in which optionally one methylene group may be replaced by oxygen, $R^3$ particularly preferably represents hydrogen, represents $C_1$–$C_4$-alkyl or represents phenyl or benzyl, each of which is optionally mono- to disubstituted by fluorine, chlorine, bromine, $C_1$–$C_4$-alkyl, $C_1$–$C_4$-alkoxy, trifluoromethyl, difluoromethoxy, trifluoromethoxy, cyano or nitro, $R^4$, $R^5$, $R^6$ each particularly preferably represent hydrogen, methyl or ethyl, $R^7$ particularly preferably represents in each case optionally fluorine- and/or chlorine-substituted $C_1$–$C_6$-alkyl, $C_2$–$C_6$-alkenyl, $C_3$–$C_6$-alkinyl, $C_1$–$C_6$-alkoxy, $C_1$–$C_4$-alkoxy-$C_1$–$C_2$-alkyl, $C_1$–$C_4$-alkylthio-$C_1$–$C_2$-alkyl, in each case optionally fluorine- and/or chlorine-, $C_1$–$C_2$-alkyl, $C_1$–$C_2$-alkoxy-substituted $C_3$–$C_6$-cycloalkyl or $C_3$–$C_6$-cycloalkoxy in which optionally one methylene group may be replaced by oxygen, represents phenyl, phenoxy, benzyloxy, thienyl, furanyl, pyridyl, pyrimidyl, thiazolyl, pyrazolyl or phenyl-$C_1$–$C_2$-alkyl, each of which is optionally mono- to disubstituted by fluorine, chlorine, bromine, $C_1$–$C_4$-alkyl, $C_1$–$C_4$-alkoxy, trifluoromethyl, difluoromethoxy, trifluoromethoxy, cyano or nitro, or, in the case of the radicals a) and c) mentioned under Ar, also represents a group

or, for the radical g), also represents hydroxyl, $R^8$ particularly preferably represents hydrogen, $R^9$ particularly preferably represents hydrogen, in each case optionally fluorine- and/or chlorine-substituted $C_1$–$C_6$-alkyl, $C_3$–$C_6$-alkenyl, $C_3$–$C_6$-alkinyl, $C_1$–$C_6$-alkoxy, $C_3$–$C_6$-cycloalkyl, in which optionally one methylene group may be replaced by oxygen, represents phenyl or phenyl-$C_1$–$C_2$-alkyl, each of which is optionally mono- to disubstituted by fluorine, chlorine, bromine, $C_1$–$C_4$-alkyl, $C_1$–$C_4$-alkoxy, trifluoromethyl, difluoromethoxy, trifluoromethoxy, cyano or nitro, $R^{10}$ particularly preferably represents hydrogen or $C_1$–$C_4$-alkyl, $R^9$, $R^{10}$ together with the nitrogen atom to which they are attached particularly preferably furthermore represent an optionally $C_1$–$C_2$-alkyl-substituted five- to six-membered cycle in which optionally one methylene group may be replaced by oxygen, m particularly preferably represents 1 to 3, n depending on m, particularly preferably represents 0 to 2, K very particularly preferably represents oxygen or sulphur.

Ar very particularly preferably represents $Ar^1$, where $Ar^1$ represents phenyl, thienyl, pyrimidyl, furanyl or pyridyl, each of which is optionally mono- to tri-substituted by fluorine, chlorine, bromine, methyl, ethyl, propyl, i-propyl, s-, n-, i- or t-butyl, methoxy, ethoxy, propoxy, i-propoxy, s-, n-, i- or t-butoxy, allyloxy, methallyloxy, 2-butenyloxy, propargyloxy, 2-butinyloxy, methylthio, ethylthio, methylsulphinyl, ethylsulphinyl, methylsulphonyl, ethylsulphonyl, trifluoromethyl, difluoromethoxy, trifluoromethoxy, methylenedioxy, difluoromethylenedioxy, tetrafluoroethylenedioxy, difluoromethylthio, trifluoromethylthio, trifluoromethylsulphinyl, trifluoromethylsulphonyl, hydroxyl, mercapto, nitro, cyano, amino or by one of the following groups a)
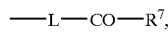
—L—CO—R⁷, b)
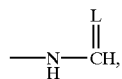

c)
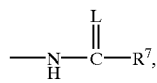

d)
NHSO₂R⁷, e)
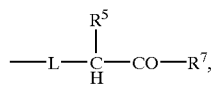

f)
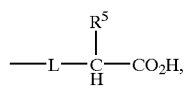

g)
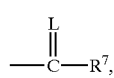

or represents Ar², where Ar² represents Ar¹ which is additionally substituted by phenyl, pyridyl, thienyl, tetrazolyl, triazolyl or phenoxy, where these substituents for their part are optionally mono- to disubstituted by fluorine, chlorine, bromine, methyl, ethyl, n- or i-propyl, s-, n-, i- or t-butyl, methoxy, ethoxy, i-propoxy, s-, n- or t-butoxy, trifluoromethyl, trifluoromethoxy, nitro or cyano, and L very particularly preferably represents oxygen or sulphur.

X very particularly preferably represents

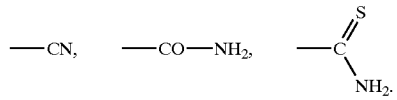
—CN,   —CO—NH₂,

Y very particularly preferably represents methyl, phenyl which is optionally mono- to tri-substituted by fluorine, chlorine, bromine, methyl, methoxy, trifluoromethyl or trifluoromethoxy, or represents the group —CO₂R¹, Two adjacent Y$_n$ may furthermore very particularly preferably represent a six-membered unsaturated cycle which may optionally be monosubstituted by fluorine, chlorine, bromine, methyl, methoxy, trifluoromethyl, trifluoromethoxy, cyano or nitro, Z very particularly preferably represents hydrogen, methyl, ethyl, allyl, propargyl, cyclopropyl, cyclopentyl, cyclohexyl, cyclopropylmethyl, cyclopentylmethyl, cyclohexylmethyl, methoxymethyl, ethoxymethyl, represents phenyl, benzyl, pyridylmethyl, thiazolylmethyl, each of which is optionally mono- to disubstituted by fluorine, chlorine, bromine, methyl, methoxy, trifluoromethyl or trifluoromethoxy, cyano or nitro, or represents the groups

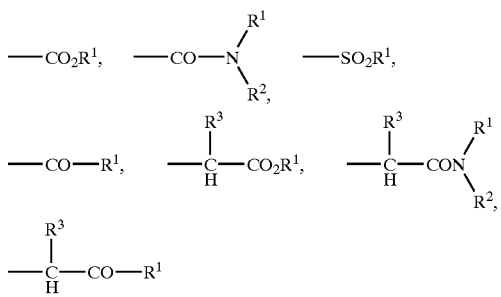

or cyano, where

R¹ very particularly preferably represents hydrogen (but not for the radicals —CO—CO₂R¹ and —SO₂R¹), methyl, ethyl, propyl, isopropyl, n-, s-, i- or t-butyl, allyl, propargyl, cyclopropyl, cyclopentyl, cyclohexyl, represents phenyl or benzyl, each of which is optionally mono- to disubstituted by fluorine, chlorine, bromine, methyl, methoxy, trifluoromethyl, trifluoromethoxy, cyano or nitro, R² very particularly preferably represents hydrogen, methyl, ethyl, propyl, isopropyl, allyl, propargyl, methoxy, ethoxy, allyloxy or represents benzyloxy which is optionally mono- to disubstituted by fluorine, chlorine, bromine, methyl, methoxy, trifluoromethyl, trifluoromethoxy, cyano or nitro, or R¹, R² together with the nitrogen atom to which they are attached very particularly preferably furthermore represent a pyrrolidine, thiazine, piperidine or morpholine radical, R³, R⁵ each very particularly preferably represent hydrogen, methyl or ethyl, R⁷ very particularly preferably represents methyl, ethyl, propyl, isopropyl, n-, s-, i- or t-butyl, vinyl, trifluoromethyl, methoxy, ethoxy, propoxy, isopropoxy, n-, s-, i- or t-butyloxy, cyclopropyl, cyclopentyl, cyclohexyl, cyclopentyloxy, cyclohexyloxy, represents phenyl, pyridyl or benzyl, each of which is optionally mono- to disubstituted by fluorine, chlorine, bromine, methyl, n-, s-, i- or t-butyl, methoxy, trifluoromethyl, trifluoromethoxy, cyano or nitro, or, in the case of the radicals a) and c) mentioned under Ar, also represents a group

or, for the radical g), also represents hydroxyl,

R⁹ very particularly preferably represents hydrogen, methyl, ethyl, propyl, isopropyl, n-, s-, i- or t-butyl, cyclopropyl, cyclopentyl, cyclohexyl, represents phenyl which is optionally mono- to disubstituted by fluorine, chlorine, bromine, methyl, methoxy, trifluoromethyl, trifluoromethoxy, cyano or nitro, R¹⁰ very particularly preferably represents hydrogen, methyl or ethyl, R⁹, R¹⁰ together with the nitrogen atom to which they are attached very particularly preferably represent a pyrrolidine, piperidine or morpholine radical.

m very particularly preferably represents 1 to 3.

n depending on m, very particularly preferably represents 0 to 1.

K most preferably represents oxygen or sulphur.

Ar most preferably represents $Ar^1$, where $Ar^1$ represents phenyl, thienyl, pyrimidyl or pyridyl, each of which is optionally mono- to tri-substituted by fluorine, chlorine, bromine, methyl, ethyl, propyl, isopropyl, n-, s-, i- or t-butyl, methoxy, ethoxy, propoxy, isopropoxy, n-, s-, i- or t-butoxy, allyloxy, methallyloxy, 2-butenyloxy, propargyloxy, 2-butinyloxy, methylthio, ethylthio, methylsulphinyl, ethylsulphinyl, methylsulphonyl, ethylsulphonyl, trifluoromethyl, difluoromethoxy, trifluoromethoxy, methylenedioxy, difluoromethylenedioxy, tetrafluoroethylenedioxy, difluoromethylthio, trifluoromethylthio, trifluoromethylsulphinyl, trifluoromethylsulphonyl, hydroxyl, nitro, mercapto, cyano, amino, or represents $Ar^2$, where $Ar^2$ represents $Ar^1$ which is additionally substituted by phenyl or phenoxy, where these substituents for their part are optionally mono- to disubstituted by fluorine, chlorine, bromine, methyl, ethyl, isopropyl, n-, s-, i- or t-butyl, methoxy, ethoxy, isopropoxy, n-, s-, i- or t-butoxy, trifluoromethyl, trifluoromethoxy, nitro or cyano.

X most preferably represents CN.

Z most preferably represents hydrogen and methyl.

m most preferably represents 1 to 3.

n most preferably represents 0.

All of the compounds of the formula (I) listed above can be present both as cis- and as trans-isomers. To simplify the presentation, in each case only one isomer was shown in the description of the compounds by formulae. However, the invention also refers to the respective other isomer.

The abovementioned general or preferred radical definitions apply both to the end products of the formula (I) and, correspondingly, to the starting materials and intermediates required in each case for the preparation. These radical definitions can be combined with one another at will, i.e. including combinations between the given preferred ranges.

Preference according to the invention is given to the compounds of the formula (I) which contain a combination of the meanings listed above as being preferred (preferable).

Particular preference according to the invention is given to the compounds of the formula (I) which contain a combination of the meanings listed above as being particularly preferred.

Very particular preference according to the invention is given to the compounds of the formula (I) containing a combination of the meanings listed above as being very particularly preferred.

Most preference according to the invention is given to the compounds of the formula (I) which contain a combination of the meanings listed above as being most preferred.

Saturated or unsaturated hydrocarbon radicals, such as alkyl or alkenyl, can in each case be straight-chain or branched, as far as this is possible, including in combination with heteroatoms, such as, for example, in alkoxy.

Unless stated otherwise, optionally substituted radicals can be mono or polysubstituted, and in the case of polysubstitutions, the substituents can be identical or different.

Examples of the compounds of the formula (I) according to the invention are listed in the groups below:

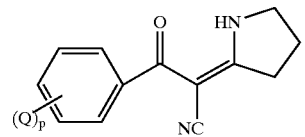

Group 1

$(Q)_p$ (p=1 to 3) has here, for example, the meanings given in the list below: fluorine, chlorine, bromine, methyl, ethyl, propyl, isopropyl, n-, s-, i- or t-butyl, methoxy, ethoxy, propoxy, isopropoxy, n-, s-, i- or t-butoxy, allyloxy, methallyloxy, 2-butenyloxy, propargyloxy, 2-butinyloxy, methylthio, ethylthio, methylsulphinyl, ethylsulphinyl, methylsulphonyl, ethylsulphonyl, trifluoromethyl, difluoromethoxy, trifluoromethoxy, methylenedioxy, difluoromethylenedioxy, tetrafluoroethylene-dioxy, difluoromethylthio, trifluoromethylthio, trifluoromethylsulphinyl, trifluoromethylsulphonyl, hydroxyl, mercapto, nitro, cyano, amino.

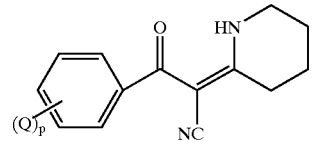

Group 2

Q and p have here, for example, the meanings given above in Group 1.

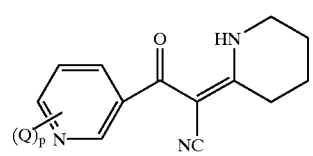

Group 3

Q and p have here, for example, the meanings given above in Group 1 (but p=0 to 2).

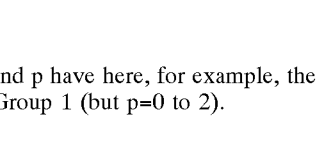

Group 4

Q and p have here, for example, the meanings given above in Group 1 (but p=0 to 2).

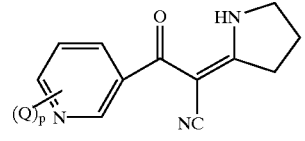

Group 5

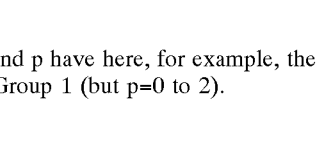

Q and p have here, for example, the meanings given above in Group 1 (but p=0 to 2).

Group 6

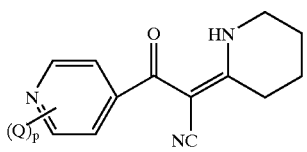

Q and p have here, for example, the meanings given above in Group 1 (but p=0 to 2).

Group 7

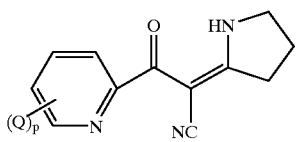

Q and p have here, for example, the meanings given above in Group 1 (but p=0 to 2).

Group 8

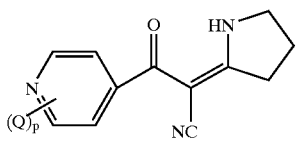

Q and p have here, for example, the meanings given above in Group 1 (but p=0 to 2).

Group 9

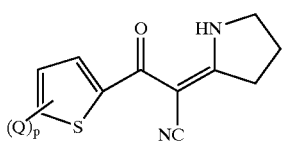

Q and p have here, for example, the meanings given above in Group 1 (but p=0 to 2).

Group 10

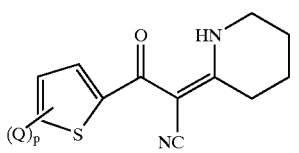

Q and p have here, for example, the meanings given above in Group 1 (but p=0 to 2).

Group 11

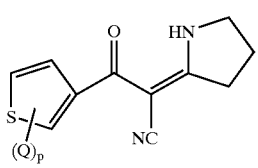

Q and p have here, for example, the meanings given above in Group 1 (but p=0 to 2).

Group 12

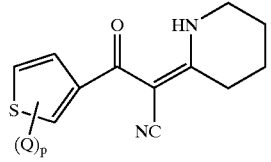

Q and p have here, for example, the meanings given above in Group 1 (but p=0 to 2).

It has been found that the novel compounds of the formula (I) are obtained by the process described below:

(A) Compounds of the formula (I)

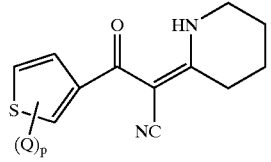 (I)

in which
Ar, X, Y, m, n are each as defined above and
K represents oxygen and
Z represents hydrogen
are obtained when
compounds of the formula (II)

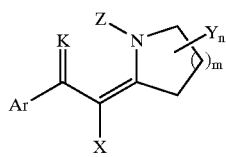 (II)

in which
Ar and X are each as defined above,
are reacted with compounds of the formula (III)

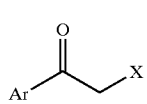 (III)

in which
Y, m, n are each as defined above and
W represents O or $S(O)_g$, where g represents 0 or 2, and
$R^{11}$ represents alkyl, in particular represents $C_1$–$C_6$-alkyl, or benzyl,
if appropriate in the presence of a diluent and if appropriate in the presence of a base or an acid and/or a metal compound of the formula (IIIa)

$Me(V)_2$ (IIIa)

in which
Me represents a divalent transition metal atom, in particular nickel, and
V represents a chelate ligand, in particular a bidentate chelate ligand, such as, for example, acetylacetonate (R. G. Glushkov et al., Khim.-Farm. Zh. 24, (7), (1990), 24–27; M. V. Mezentseva et al., Khim.-Farm. Zh. 25,(12), (1991), 19–23; G. Dannhardt, A. Bauer, Pharmazie 51,(1996), 805–810).

(B) Moreoveer, it has been found that compounds of the formula (I)

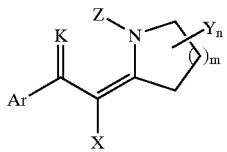
(I)

in which
Ar, Y, X, m, n are each as defined above and
K represents oxygen and
Z represents hydrogen,
are obtained when compounds of the formula (IV)

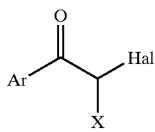
(IV)

in which
Ar and X are each as defined above and
Hal represents halogen, in particular chlorine or bromine,
are reacted with compounds of the formula (V)

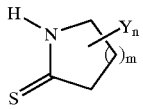
(V)

in which
Y, m and n are each as defined above,
if appropriate in the presence of a diluent, to give compounds of the formula (VI)

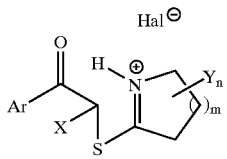
(VI)

in which
Ar, X, Y, m and n are each as defined above,
which are reacted further, if appropriate in the presence of a base and if appropriate in the presence of a trivalent phosphorus compound (for example triphenylphosphine, triethyl phosphite) with elimination of sulphur and hydrogen halide, to give compounds of the formula (I),
in which
Ar, X, Y, m and n are each as defined above and
Z represents hydrogen (see A. Eschenmoser et al., Helv. Chim. Acta 54, (1971), 710–734; V. Issartel et al., C.R. Acad. Sci., Ser. II, Mec., Phys., Chim., Astron. 321, (12), (1995), 521–524).

(C) Furthermore, it has been found that compounds of the formula (I)

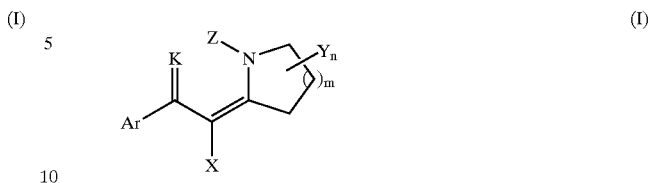
(I)

in which
Ar, Z, X, Y, m and n each have one of the meanings given above and
K represents oxygen but
Z does not represent hydrogen, are obtained when compounds of the formula (VII)

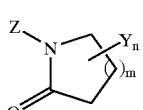
(VII)

in which
Y, Z, m and n
each have one of the meanings given above
and Z does not represent hydrogen,
are reacted with halogenating agents, such as, for example, phosgene, diphosgene and triphosgene, if appropriate in the presence of a diluent, to give compounds of the formula (VIII)

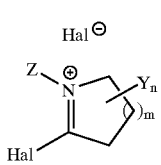
(VIII)

in which
Y, Z, m and n each have one of the meanings given above
and Z does not represent hydrogen and
Hal represents halogen, in particular chlorine or bromine,
which are then reacted with compounds of the formula (II)

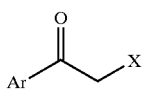
(II)

in which
Ar, X are each as defined above,
if appropriate in the presence of a diluent and if appropriate in the presence of an acid acceptor (see G. Dannhardt, A. Bauer, Pharmazie 51, (1996), 805–810).

(D) Furthermore, it has been found that compounds of the formula (I)

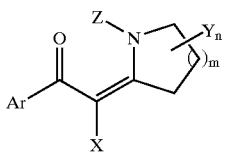
(I)

in which
Ar, Z, X, Y, m and n each have one of the meanings given above and
K represents oxygen, but
Z does not represent hydrogen,
are obtained when
compounds of the formula (I-a)

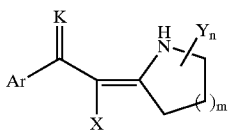
(I-a)

in which
Ar, X, Y, m and n are each as defined above,
are reacted with alkylating agents, acylating agents, sulphonylating agents or condensing agents of the formula (IX)

Z—G     (IX), in which
G represents a leaving group, such as halogen, in particular iodine, bromine, chlorine, sulphonate, such as, for example, mesylate, triflate or toluenesulphonate, or alkoxy,
if appropriate in the presence of a solvent and if appropriate in the presence of a base.

(E) Moreover, it has been found that compounds of the formula (I)

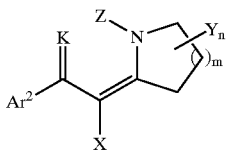
(I)

in which
$Ar^2$, X, Y, Z, m and n are each as defined above and
K represents oxygen,
are obtained when compounds of the formula (II)

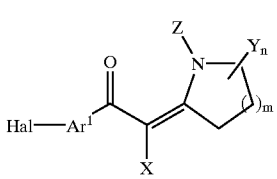
(I¹)

in which
$Ar^1$, X, Y, Z, m and n are each as defined above and
Hal represents halogen, in particular bromine, are reacted with boronic acids of the formula (X)

$Ar^{2'}$—$B(OH)_2$     (X), in which
$Ar^{2'}$ represents the substituents which have been mentioned above under $Ar^2$ as additional substituents for $Ar^1$,
in the presence of a solvent, if appropriate in the presence of a base and a noble metal complex, preferably a palladium complex.

(F) Furthermore, it has been found that compounds of the formula (I)

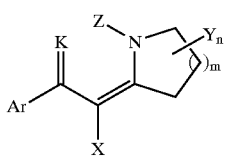
(I)

in which
Ar, X, Y, Z, m and n are each as defined above and
K represents sulphur,
are obtained when compounds of the formula (I)

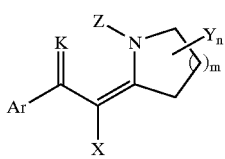
(I)

in which
Ar, X, Y, Z, m and n are each as defined above and
K represents oxygen,
are reacted in the presence of a sulphurizing agent, such as, for example, phosphorus pentasulphide or 2,4-bis-(4-methoxyphenyl)-1,2,3,4-dithiaphosphetane-2,4-disulphide (Lawesson's reagent), in the presence of a solvent.

Using, according to process A, for example 4-methyl-benzoylacetonitrile and 2-methoxy-1-pyrroline as starting materials, the course of the reaction can be represented by the following reaction scheme:

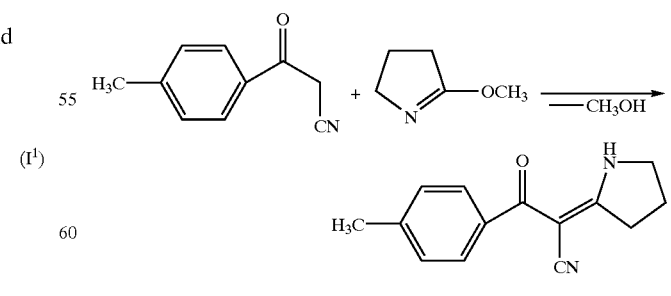

Using, according to process B, for example 2-bromo-2-(3-chlorobenzoyl)acetonitrile and pyrrolidine-2-thione as starting materials, the course of the reaction can be represented by the following reaction scheme:

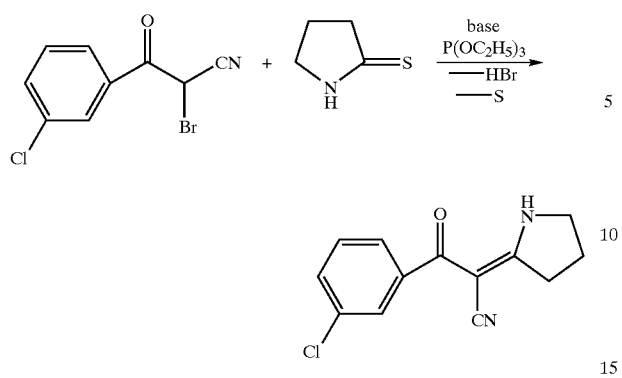

Using, according to process C, for example 3,4-dichlorobenzoyl-acetonitrile and N-methyl-pyrrolidone as starting materials, the course of the reaction can be represented by the following reaction scheme:

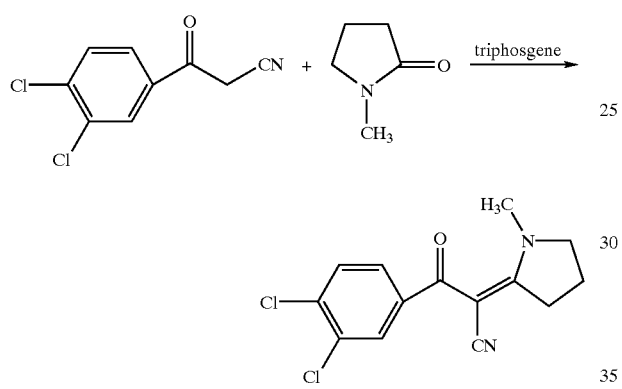

Using, according to process D, for example 3-oxo-2-pyrrolidin-2-ylidene-3-(4-trifluoromethoxy-phenyl)-propionitrile and 2-chloro-5-chloromethyl-pyridine as starting materials, the course of the reaction can be represented by the following reaction scheme:

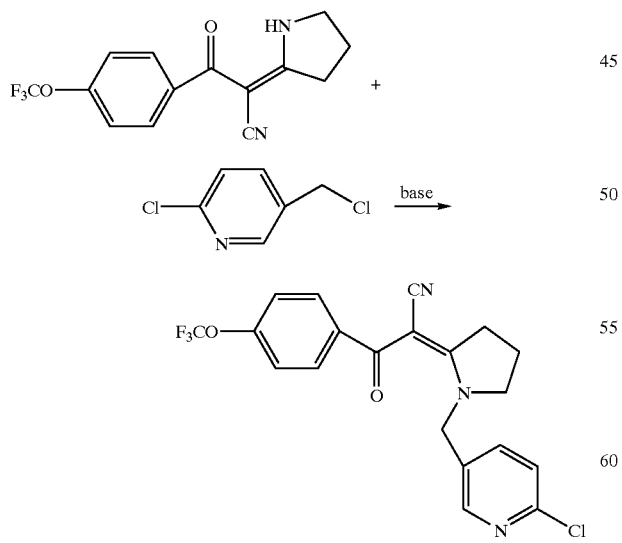

Using, according to process D, for example 3-oxo-2-pyrrolidin-2-ylidene-3-(4-tri-fluoromethyl-phenyl)-propionitrile and 4-chlorobenzoyl chloride as starting materials, the course of the reaction can be represented by the following reaction scheme:

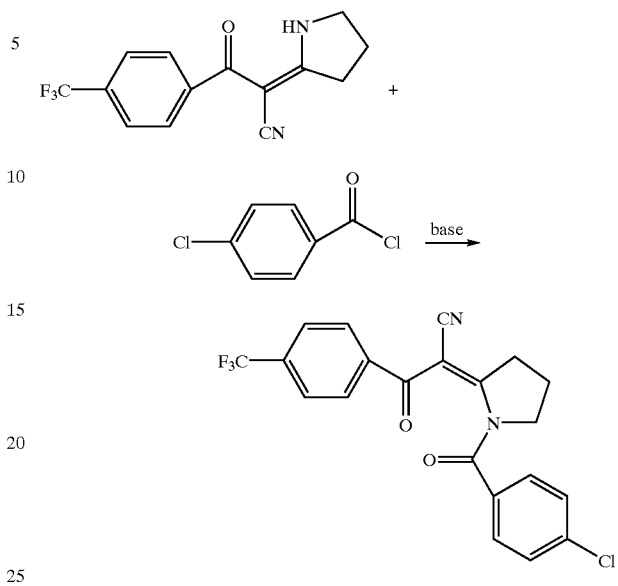

Using, according to process E, for example 3-oxo-2-pyridin-2-ylidene-3-(4-bromo-phenyl)-propionitrile and 4-chloro-phenylboronic acid as starting materials, the course of the reaction can be represented by the following reaction scheme:

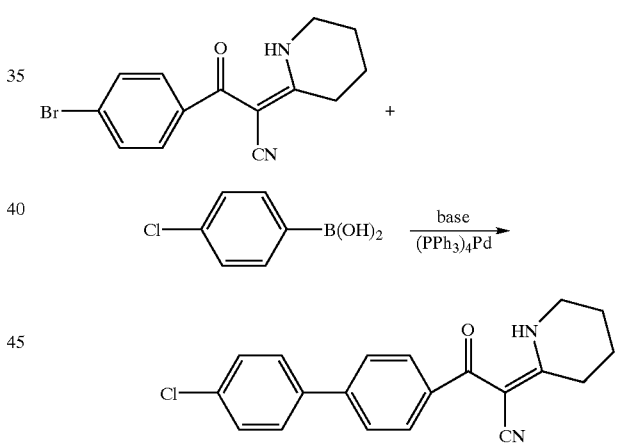

Using, according to process F, for example 3-oxo-2-pyrrolidine-3-(4-chlorophenyl)propionitrile as starting material and Lawesson's reagent, the course of the reaction can be represented by the following reaction scheme:

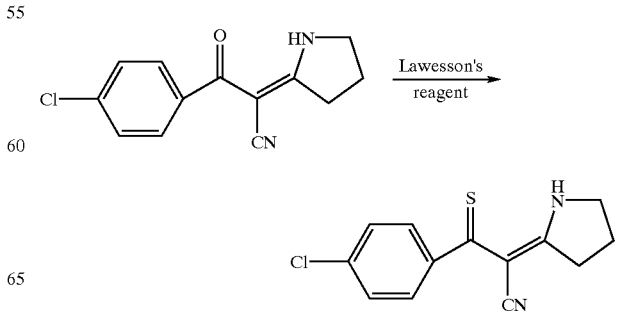

Some of the compounds of the formula (II)

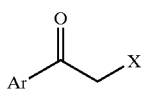
(II)

in which

Ar, X are each as defined above, required as starting materials in the process (A) are novel and can be prepared by processes known in principle from the literature (Organikum, 16$^{th}$ revised edition, pp. 415, 417, VEB Deutscher Verlag der Wissenschaften, Berlin 1986).

From among the compounds of the formula (II), the novel compounds of the formula (II-1-b),

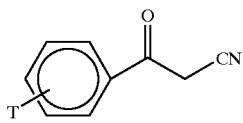
(II-1-b)

where

T is as defined in the table below:

| Comp. No. | T | M.p. ° C. |
|---|---|---|
| II-1-b-1 | 3-Cl, 4-F | 78 |
| II-1-b-2 | 4-Cl, 3-F | 87 |
| II-1-b-3 | 3,5-(CF$_3$)$_2$ | 91 |
| II-1-b-4 | 2,4-Cl$_2$, 5-F | 106 |
| II-1-b-5 | 3,5-Cl$_2$, 4-F | 138–140 |
| II-1-b-6 | 4-Cl, 2-F | 90–94 |
| II-1-b-7 | 3-CF$_3$, 5-CH$_3$ | 92 |
| II-1-b-8 | 3-Cl, 4,5-F$_2$ | 84–88 |
| II-1-b-9 | 4-CN, 2,5-F$_2$ | 107–108 |
| II-1-b-10 | 2,3-F$_2$ | 74 |
| II-1-b-11 | 3-F, 4-CF$_3$ | 92 |
| II-1-b-12 | 3,4-O—CF$_2$—O | 70–73 |
| II-1-b-13 | 3-NO$_2$, 5-CF$_3$ | |
| II-1-b-14 | 4-Cl, 2,5-F$_2$ | 116 |
| II-1-b-15 | 3,4,5-(OC$_2$H$_5$)$_3$ | 122 |
| II-1-b-16 | 4-Br, 2-F | 118 |
| II-1-b-17 | 2,6-Cl$_2$, 4-CF$_3$ | 123 |
| II-1-b-18 | 2-F, 4-NO$_2$ | 168 |
| II-1-b-19 | 2,4-Cl$_2$, 5-NO$_2$ | 100 |
| II-1-b-20 | 4-Cl, 2-F, 5-NO$_2$ | 118 |
| II-1-b-21 | 2,4-F$_2$, 5-NO$_2$ | 128 |
| II-1-b-22 | 4-Br, 2-F, 5-NO$_2$ | 141 |
| II-1-b-23 | 2-F, 4-CF$_3$ | 62 |
| II-1-b-24 | 4-OCF$_3$, 3-NO$_2$ | 95 |
| II-1-b-25 | 4-Cl, 2-NO$_2$ | 130 |
| II-1-b-26 | 2-F, 3-CF$_3$ | 67–69 |
| II-1-b-27 | 2-Cl, 6-F | 46–48 |
| II-1-b-28 | 2-Cl, 3-CF$_3$ | 90–93 |
| II-1-b-29 | 3,4-O—(CF$_2$)$_2$—O— | 206 |
| II-1-b-30 | 2-Cl, 4-SCH$_3$ | 110 |
| II-1-b-31 | 2-Cl, 4-SO$_2$CH$_3$ | 202 | and the compound of the formula (II-2-b)

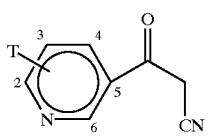
(II-2-b)

where T is as defined in the table below:

| Comp. No. | T | M.p. ° C. |
|---|---|---|
| II-2-b-1 | 2,6-Cl$_2$ | >220 |
| II-2-b-2 | 2,6-Cl$_2$, 4-CH$_3$ | 95 |
| II-2-b-3 | 6-Cl | 122 | and the compound of the formula (II-3-b)

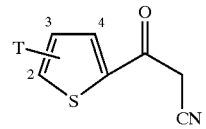
(II-3-b)

where T is as defined in the table below:

| Comp. No. | T | M.p. ° C. |
|---|---|---|
| II-3-b-1 | 2-CF$_3$, 3-(4-Cl'—C$_6$H$_4$) | oil |
| II-3-b-2 | 2-CF$_3$, 3-(2,4-Cl$_2$'—C$_6$H$_3$) | oil | and the compound No. II-4-b-1

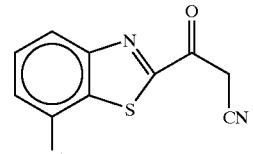

Comp. No. II-4-b-1; M.p. 241° C.
and the compound N. II-5-b-1

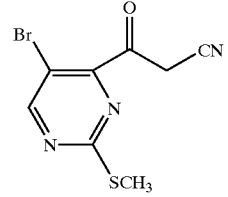

Comp. No. II-5-b-1, resin
are particularly suitable for preparing novel pesticidal, in particular acaricidal, herbicidal and insecticidal end products.

The compounds of the formula (II) are obtained, for example, by hydrolysing and then decarboxylating compounds of the formula (XI)

$$\underset{\underset{CN}{|}}{Ar-\overset{O}{\underset{}{C}}-CH-\overset{O}{\underset{}{C}}-O-R^{12}}$$
(XI)

in which

Ar is as defined above,

R$^{12}$ represents alkyl, in particular C$_1$–C$_6$-alkyl, or benzyl, which may optionally be substituted, in the presence of an acid (for example an inorganic acid, such as hydrogen chloride) or a base (for example an alkali metal hydroxide, such as sodium hydroxide or potassium hydroxide) and, if appropriate, in the presence of a diluent (for example an aqueous alcohol, such as methanol or ethanol) at temperatures between 0° C. and 200° C., preferably between 20° C. and 150° C., where the removal of the radical $R^{12}$ may, if desired, also be effected hydrolytically by known processes (Bowman, Fordham, J. Chem. Soc. 1951, 2758) using molecular hydrogen at pressures between 1 and 100 bar, if appropriate in the presence of a solvent, such as, for example, methanol, ethanol or ethyl acetate, at temperatures between −20 and 100° C., preferably at room temperature, in the presence of a transition metal, such as, for example, palladium, nickel, rhodium or platinum, which is, if appropriate, immobilized on a carrier, such as, for example, activated carbon or barium sulphate.

The compounds of the formula (XI) can be prepared by known processes (Organikum, $16^{th}$ revised edition, p. 480, VEB Deutscher Verlag der Wissenschaften, Berlin 1986).

The compounds of the formula (XI) are obtained, for example, by reacting compounds of the formula (XII)

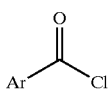

(XII)

in which
Ar is as defined above,
with cyanoacetates of the formula (XIII)

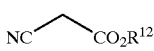

(XIII)

in which
$R^{12}$ represents alkyl, in particular $C_1$–$C_6$-alkyl,
in the presence of a base (for example a metal alkoxide, such as sodium methoxide or sodium ethoxide) and, if appropriate, in the presence of a diluent (for example ether or the alcohol derived from the alkoxide), at temperatures from 0° C. to 150° C., preferably between 20° C. and 120° C.

Some of the compounds of the formula (XII) are novel and can be prepared by processes known in principle (for example Organikum, $16^{th}$ revised edition, p. 423, VEB Deutscher Verlag der Wissenschaften, Berlin 1986).

The compounds of the formula (XII) are obtained, for example, by reacting compounds of the formula (XIV)

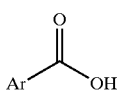

(XIV)

in which
Ar is as defined above,
with halogenating agents (for example thionyl chloride, phosgene, phosphorus trichloride), if appropriate in the presence of a diluent (for example optionally chlorinated aliphatic or aromatic hydrocarbons, such as toluene or methylene chloride), at temperatures of from 0° C. to 150° C., preferably between 20° C. and 100° C.

Cyanoacetates of the formula (XIII) are known compounds of organic chemistry.

The compounds of the formula (III)

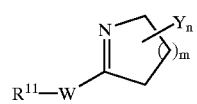

(III)

in which
Y, $R^{11}$, m and n are each as defined above and
W represents oxygen,
also required as starting materials for the process (A) can be prepared by known processes (Pendrak et al., J. Org. Chem. 60, (1995), 2912–2915).

The compounds of the formula (III) are obtained, for example, by reacting compounds of the formula (VII)

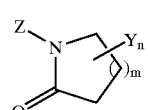

(VII)

in which
Y, m and n are each as defined above and
Z represents hydrogen,
with alkylating agents (for example dimethyl sulphate, triethyloxonium tetra fluoroborate (Meerwein salt)), at temperatures of from −20° C. to 150° C., preferably of from 0° C. to 100° C., if appropriate in the presence of a diluent.

The compounds of the formula (III)

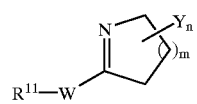

(III)

in which
Y, $R^{11}$, m, n are each as defined above and
W represents sulphur,
required as starting materials for the process A are furthermore obtained when compounds of the formula (VII)

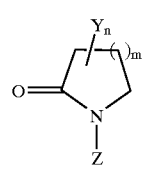

(VII)

in which
Y, m and n are each as defined above and
Z represents hydrogen
are initially converted with a sulphurizing reagent, for example Lawesson's reagent, into the thioamide of the formula (V)

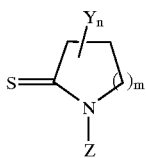

in which
Y, m and n are each as defined above and Z represents hydrogen
in the presence of a solvent, and subsequently reacted with an alkylating agent of the formula (XV), $$R^{11}-Hal \qquad (XV)$$

in which
$R^{11}$ is as defined above and
Hal represents halogen, in particular iodine and bromine,
if appropriate in the presence of a base and if appropriate in the presence of a solvent.

The process (A) is characterized in that compounds of the formula (II)
in which
Ar, X are each as defined above,
and compounds of the formula (III)
in which
$R^{11}$, W, Y, m, n are each as defined above,
are reacted in the presence of a diluent and, if appropriate, in the presence of a base.

Suitable diluents for the process (A) are all organic solvents which are inert towards the reactants. Preference is given to using optionally chlorinated aliphatic or aromatic hydrocarbons, such as toluene, xylene or methylene chloride, and furthermore polar solvents, such as dimethyl sulphoxide, dimethylformamide or N-methylpyrrolidone.

Suitable bases for carrying out the process (A) are all customary acid acceptors which do not hydrolyse the reactants.

Preference is given to using tertiary amines, such as triethylamine, pyridine or N,N-dimethylaniline.

Suitable acids for carrying out process (A) are all acids which do not hydrolyse the reactants. Preference is given to using organic acids, such as p-toluenesulphonic acid and trifluoroacetic acid.

When carrying out the process (A), the reaction temperature can be varied within a relatively wide range. Advantageously, the process is carried out at temperatures between −20° C. and 160° C., preferably between 0° C. and 120° C.

The process (A) is preferably carried out under atmospheric pressure.

When carrying out the process (A), the reaction components of the formula (III) are employed in an equimolar amount or in a relatively large excess (up to 5 mol), preferably in 1.5 to 2 times the molar amount, based on the reaction component of the formula (II).

The base which is used, if appropriate, is preferably employed in an equimolar amount to the reaction component of the formula (II). The acid which is used, if appropriate, is preferably employed in catalytic amounts.

The process (B) is characterized in that compounds of the formula (IV) are in each case reacted with thioamide of the formula (V), if appropriate in the presence of a diluent and if appropriate in the presence of an acid binder.

The starting materials of the formula (IV) can be prepared by known processes (Gakhar H. K. et al., J. Indian Chem. Soc. 43, (1971), 953 or Corsaro A., Heterocycles 23, (1985), 2645). The compounds of the formula (V) can be prepared from the corresponding keto compound using thionylating agents, in particular Lawesson's reagent, in inert solvents, such as, for example, toluene (see Preparation Example 9). With the exception of 5-phenyl-pyrrolidine-2-thione (see Lettau et at. PHARAT, Pharmazie 48 (1993) 410) and 5-(3,4-dimethoxy-phenyl)-pyrrolidine-2-thione, the substituted 5-phenyl-pyrrolidone-2-thiones and 6-phenyl-piperidine-2-thiones of the formula (V) are novel.

Suitable diluents for the process (B) according to the invention are all solvents which are inert towards the compounds of the formula (IV). Preference is given to using hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethylformamide, N-methylpyrrolidone, dimethylsulphoxide and sulpholane.

Suitable acid binders for the reaction according to process (B) according to the invention are all customary acid acceptors. Preference is given to using tertiary amines, such as triethylamine, pyridine, diazabicyclooctane (DABCO), diazabicycloundecene (DBU), diazabicyclononene (DBN), Huinig base and N,N-dimethylaniline, polymeric bases, such as diisopropylaminopolystyrene, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

Suitable phorphorus reagents for the process (B) according to the invention are alkyl phosphites, such as triethyl phosphite, tributyl phosphite, or triphenylphosphines, such as triphenylphosphine.

When carrying out the process (B) according to the invention, the reaction temperature can be varied within a relatively wide range. In general, the process is carried out at temperatures between −0° C. and 200° C., preferably between 20° C. and 150° C.

When carrying out the process (B) according to the invention, the reaction temperature can be varied within a relatively wide range. In general, the process is carried out at temperatures between 0° C. and 200° C., preferably between 20° C. and 150° C.

When carrying out the process (B) according to the invention, the starting materials of the formula (IV) and the thioamide of the formula (V) are generally in each case employed in approximately equivalent amounts. However, it is also possible to use a relatively large excess of one or the other component. Work-up is carried out by customary methods.

The process (C) is characterized in that compounds of the formula (VII) are reacted with halogenating agents, such as, for example, phosgene, diphosgene, triphosgene, if appropriate in the presence of a diluent, to give compounds of the formula (VIII) which are then reacted with compounds of the formula (II), if appropriate in the presence of an acid binder and if appropriate in the presence of a diluent. Some of the starting materials of the formula (VII), such as, for example, N-methyl-pyrrolidone, are commercially available, or they can be prepared by known processes.

Suitable acid binders for the reaction according to the process (C) according to the invention are all customary acid acceptors. Preference is given to using tertiary amines, such as triethylamine, pyridine, diazabicyclooctane (DABCO), diazabicycloundecene (DBU), diazabicyclononene (DBN), Hunig base and N,N-dimethylaniline, polymeric bases, such as, for example, diisopropylaminopolystyrene, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

Suitable diluents for the process (C) according to the invention are all solvents which are inert towards the halogenating agents. Preference is given to using hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, moreover nitrites, such as acetonitrile, and also strongly polar solvents, such as dimethyl sulphoxide and sulpholane.

When carrying out the process (C) according to the invention, the reaction temperature can be varied within a relatively wide range. In general, the process is carried out at temperatures between −20° C. and 100° C., preferably between 0° C. and 80° C.

The process (C) according to the invention is generally carried out under atmospheric pressure.

When carrying out the process (C) according to the invention, the starting materials of the formula (VII) and the appropriate halogenating agent are generally in each case employed in approximately equivalent amounts. However, it is also possible to use a relatively large excess (up to 3 mol) of one or the other component. Work-up is carried out by customary methods. In general, precipitated salts are removed and the reaction mixture that remains is concentrated by stripping off the diluent.

The process (D) is characterized in that compounds of the formula (I) in which Ar, X, Y, m and n are each as defined above and Z represents hydrogen are in each case reacted with alkylating agents, acylating agents, sulphonylating agents or condensing agents of the formula (IX), if appropriate in the presence of a diluent and if appropriate in the presence of an acid binder.

The alkylating agents, acylating agents, sulphonylating agents or condensing agents of the formula (IX) to be used are known synthesis chemicals of organic chemistry.

Suitable diluents for the process (D) according to the invention aree all solvents which are inert towards the abovementioned reagents. Preference is given to using hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents such as, for example, dimethyl sulphoxide, dimethylformamide, N-methylpyrrolidone and sulpholane. The hydrolytic stability of the acylating agents and sulphonylating agents permitting, the reaction can also be carried out in the presence of water.

Suitable acid binders for the reaction according to the process (D) according to the invention are all customary acid acceptors. Preference is given to using tertiary amines, such as triethylamine, pyridine, diazabicyclooctane (DABCO), diazabicycloundecene (DBU), diazabicyclononene (DBN), Hünig base and N,N-dimethylaniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide, and furthermore alkali metal hydrides, such as sodium hydride, potassium hydride, or alkali metal alkoxides, such as potassium tert-butoxide.

When carrying out the process (D) according to the invention, the reaction temperatures can be varied within a relatively wide range. In general, the process is carried out at temperatures between −70° C. and +150° C., preferably between −20° C. and 100° C.

When carrying out the process (D) according to the invention, the abovementioned starting materials of the formula (I) and the abovementioned reagents of the formula (IX) are generally in each case employed in approximately equivalent amounts. However, it is also possible to use a relatively large excess (up to 5 mol) of the abovementioned reagents. Work-up is carried out by customary methods.

Preferred catalysts for carrying out the process (E) according to the invention are palladium(0) complexes. Preference is given, for example, to tetrakis (triphenylphosphine)palladium.

Some of the arylboronic acids required for carrying out the process (E) are commercially available, such as, for example, 4-chloro-phenylboronic acid, or they can be prepared by known processes.

Suitable acid acceptors for carrying out the process (E) according to the invention are inorganic or organic bases. These preferably include alkaline earth metal or alkali metal hydroxides, acetates, carbonates or bicarbonates, such as, for example, sodium hydroxide, potassium hydroxide, barium hydroxide or ammonium hydroxide, sodium acetate, potassium acetate, calcium acetate or ammonium acetate, sodium carbonate, potassium carbonate or ammonium carbonate, sodium bicarbonate or potassium bicarbonate, alkali metal fluorides, such as, for example, caesium fluoride, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicycloundecene (DBU), diazabicyclononene (DBN).

Suitable diluents for carrying out the process (E) according to the invention are water, organic solvents and any mixtures of these. Examples which may be mentioned are: aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, methylene chloride, chloroform, carbon tetrachloride, dichloroethane, trichloroethane or tetrachloroethylene; ethers, such as diethyl ether, diisopropyl ether, methyl tert-butyl ether, methyl tert-amyl ether, dioxane, tetrahydrofuran, 1,2-dimethoxyethane, 1,2-diethoxyethane, diethylene glycol dimethyl ether or anisole; alcohols, such as methanol, ethanol, n- or i-propanol, n-, iso-, sec- or tert-butanol, ethane-diol, propane-1,2-diol, ethoxyethanol, methoxyethanol, diethylene glycol monomethyl ether, diethylene glycol monoethyl ether; water.

When carrying out the process (E) according to the invention, the reaction temperatures can be varied within a relatively wide range. In general, the process is carried out at temperatures between 0° C. and +140° C., preferably between 50° C. and +100° C.

When carrying out the process (E) according to the invention, the boronic acid of the formula (X) in which $Ar^{2\prime}$ is as defined above and compounds of the formula ($I^1$) in which $Ar^1$, X, Y, Z, m, n and Hal are each as defined above are employed in a molar ratio of from 1:1 to 3:1, preferably from 1:1 to 2:1, In general from 0.005 to 0.5 mol, preferably from 0.01 to 0.1 mol, of catalyst are employed per mole of the compound of the formula ($I^1$). The base is generally employed in excess.

The process (F) is characterized in that compounds of the formula (I) in which Ar, X, Y, Z, m and n are each as defined above and K represents oxygen are reacted with sulphurizing agents, if appropriate in the presence of a diluent.

The sulphurizing agents to be used are known chemicals for synthesis such as, for example, phosphorus pentasulphide or 2,4-bis-(4-methoxyphenyl)-1,2,3,4-dithiaphosphetane-2,4-disulphide (Lawesson's reagent).

Suitable diluents for the process (F) according to the invention are all solvents which are inert towards the abovementioned reagents. Preference is given to using hydrocarbons, such as, for example, benzine, benzene, toluene, xylene and tetralin, furthermore halogenated hydrocarbons, such as methylene chloride, chloroform, chlorobenzene and o-dichlorobenzene, ethers, such as tetrahydrofuran, dioxane, diisopropyl ether or methyl tert-butyl ether.

When carrying out process (F) according to the invention, the reaction temperatures can be varied within a relatively wide range. In general, the process is carried out at temperatures between 0° C. and 250° C., preferably between 40° C. and 200° C.

When carrying out the process (F) according to the invention, the starting materials of the formula (I) and the abovementioned reagents are generally in each case employed in approximately equivalent amounts. However, it is also possible to employ a relatively large excess of up to 5 mol of the abovementioned reagents. Work-up is carried out by customary methods.

The active compounds according to the invention are particularly suitable for use as defoliants, desiccants, haulm-killers and, especially, as weed-killers. By weeds, in the broadest sense, are to be understood all plants which grow in locations where they are undesired. Whether the substances according to the invention act as total or selective herbicides depends essentially on the amount used.

The dosages of the active compounds according to the invention required for weed control are between 0.001 and 10 kg/ha, preferably between 0.005 and 5 kg/ha.

The active compounds according to the invention can be used, for example, in connection with the following plants:

Dicotyledonous weeds of the genera: Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, H-ibiscus, Ipomoea, Kochia, Lamium, Lepidium, Lindemia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.

Dicotyledonous crops of the geneera: Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia.

Monocotyledonous weeds of the genera: Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.

Monocotyledonous crops of the genera: Allium, Ananas, Asparagus, Avena, Hordeum, Oryza, Panicum, Saccharum, Secale, Sorghum, Triticale, Triticum, Zea.

According to the invention, it is possible to treat all plants and parts of plants. By plants are to be understood here all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by plant breeders certificates. Parts of plants are to be understood as meaning all above-ground and below-ground parts and organs of plants, such as shoot, leaf, flower and root, examples which may be mentioned being leaves, needles, stems, trunks, flowers, shoot-bodies, fruits and seeds and also roots, tubers and rhizomes. Parts of plants also include harvested plants and vegetative and generative propagation material, for example seedlings, tubers, rhizomes, cuttings and seeds.

The treatment of the plants and parts of plants according to the invention with the active compounds is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multi-layer coating.

However, the use of the active compounds according to the invention is in no way restricted to these generea, but also extends in the same manner to other plants. In the use of the active compounds according to the invention, particular emphasis is given to the use in connection with transgenic plants, since in this case synergistic activity increases may be observed.

The compounds are suitable, depending on the concentration, for the total control of weeds, for example on industrial terrain and rail tracks, and on paths and squares with or without tree plantings. Equally, the compounds can be employed for controllling weeds in perennial cultures, for example forests, decorative tree plantings, orchards, vineyards, citrus groves, nut orchards, banana plantations, coffee plantations, tea plantations, rubber plantations, oil palm plantations, cocoa plantations, soft fruit plantings and hopfields, on lawns, turf and pasture-land, and for the selective control of weeds in annual crops.

The active compounds according to the invention are highly suitable for the selective control of monocotyledonous weeds in dicotyledonous crops by the pre- and post-emergence method. They can be used very successfully, for example, for the control of harmful grasses in cotton or sugar beet.

The active compounds can be converted into the customary formulations, such as solutions, emulsions, wettable powders, suspensions, powders, dusting agents, pastes, soluble powders, granules, suspo-emulsion concentrates, natural and synthetic materials impregnated with active compound and very fine capsules and polymeric substances.

These formulations are prepared in a known manner, for example by mixing the active compounds with extenders, that is liquid solvents and/or solid carriers, if appropriate with the use of surfactants, that is emulsifiers and/or dispersants and/or foam-formers.

If the extender used is water, it is also possible to use, for example, organic solvents as auxiliary solvents. Suitable liquid solvents are essentially: aromatics, such as xylene, toluene, or alkylnaphthalenes, chlorinated aromatics and chlorinated aliphatic hydrocarbons, such as chlorobenzene, chloroethylenes or methylene chloride, aliphatic hydrocarbons, such as cyclohexane or paraffins, for example mineral oil fractions, mineral or vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethylsulphoxide, and also water.

Suitable solid carriers are:
  for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95% by weight of active compound, preferably between 0.5 and 90%, and in addition extenders and/or surfactants.

The active compound according to the invention can be present in its commercially available formulations and in the use forms, prepared from these formulations, as a mixture with other active compounds, such as insecticides, attractants, sterilizing agents, bactericides, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia. In preferred embodiments of the present invention, it is also possible to mix safeners with the compounds according to the invention, to increase crop plant compatibility.

Examples of particularly advantageous mixing components are the following:
Fungicides:
  aldimorph, ampropylfos, ampropylfos potassium, andoprim, anilazine, azaconazole, azoxystrobin,
  benalaxyl, benodanil, benomyl, benzamacril, benzamacril-isobutyl, bialaphos, binapacryl, biphenyl, bitertanol, blasticidin-S, bromuconazole, bupirimate, buthiobate,
  calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram,
  debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon,
  edifenphos, epoxiconazole, etaconazole, ethirimol, etridiazole,
  famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazolecis, furmecyclox,
  guazatine,
  hexachlorobenzene, hexaconazole, hymexazole,
  imazalil, imibenconazole, iminoctadine, iminoctadine albesilate, iminoctadine triacetate, iodocarb, ipconazole, iprobenfos (IBP), iprodione, irunamycin, isoprothiolane, isovaledione,
  kasugamycin, kresoxim-methyl, copper preparations, such as: copper hydroxide, copper naphthenate, copper oxychloride, copper sulphate, copper oxide, oxine-copper and Bordeaux mixture,
  mancopper, mancozeb, maneb, meferimzone, mepanipyrim, mepronil, metalaxyl, metconazole, methasulfocarb, methfuroxamn, metiram, metomeclamn, metsulfovax, mildiomycin, myclobutanil, myclozolin,
  nickel dimethyldithiocarbamate, nitrothal-isopropyl, nuarimol,
  ofurace, oxadixyl, oxamocarb, oxolinic acid, oxycarboxim, oxyfenthiin,
  paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur,
  quinconazole, quintozene (PCNB),
  sulphur and sulphur preparations,
  tebuconazole, tecloftalam, tecnazene, tetcyclacis, tetraconazole, thiabendazole, thicyofen, thifluzamide, thiophanatemethyl, thiram, tioxymid, tolclofos-methyl, tolylfluanid, triadimefon, triadimenol, triazbutil, triazoxide, trichlamide, tricyclazole, tridemorph, triflumizole, triforine, triticonazole, uniconazole, validamycin A, vinclozolin, viniconazole, zarilamide, zineb, ziram and also Dagger G,

OK-8705,

OK-8801,

∀-(1,1-dimethylethyl)-∃-(2-phenoxyethyl)-1H-1,2,4-triazole-1-ethanol,

∀-(2,4-dichlorophenyl)-∃-fluoro-∃-propyl-1H-1,2,4-triazole-1-ethanol,

∀-(2,4-dichlorophenyl)-∃-methoxy-∀-methyl-1H-1,2,4-triazole-1-ethanol,

∀-(5-methyl-1,3-dioxan-5-yl)-3-[[4-(trifluoromethyl)phenyl]methylene]1H-1,2,4-triazole-1-ethanol, (5RS,6RS)-6-hydroxy-2,2,7,7-tetramethyl-5-(1H-1,2,4-triazol-1-yl)-3-octanone, (E)-∀-(methoxyimino)-N-methyl-2-phenoxy-phenylacetamide, 1-isopropyl {2-methyl-1-[[[1-(4-methylphenyl)ethyl]amino]carbonyl]propyl}-carbamate, 1-(2,4-dichlorophenyl)-2-(1H-1,2,4-triazol-1-yl)-ethanone O(phenylmethyl)-oxime, 1-(2-methyl-1-naphthalenyl)-1H-pyrrole-2,5-dione, 1-(3,5-dichlorophenyl)-3-(2-propenyl)-2,5-pyrrolidinedione, 1-[(diiodomethyl)sulphonyl]-4-methyl-benzene, 1-[[2-(2,4-dichlorophenyl)-1,3-dioxolan-2-yl]-methyl]-1H-imidazole, 1-[[2-(4-chlorophenyl)-3-phenyloxiranyl]-methyl]-1H-1,2,4-triazole, 1-[1-[2-[(2,4-dichlorophenyl)methoxy]-phenyl]-ethenyl]-1H-imidazole, 1-methyl-5-nonyl-2-(phenylmethyl)-3-pyrrolidinole, 2'6'-dibromo-2-methyl-4'-trifluoromethoxy-4'-trifluoro-methyl-1,3-thiazole-5-carboxanilide, 2,2-dichloro-N-[1-(4-chlorophenyl)-ethyl]-1-ethyl-3-methyl-cyclopropanecarboxamide, 2,6-dichloro-5-(methylthio)-4-pyrimidinyl-thiocyanate, 2,6-dichloro-N-(4-trifluoromethylbenzyl)-benzamide, 2,6-dichloro-N-[[4-(trifluoromethyl)-phenyl]-methyl]-benzamide, 2-(2,3,3-triiodo-2-propenyl)-2H-tetrazole, 2-[(1-methylethyl)sulphonyl]-5-(trichloromethyl)-1,3,4-thiadiazole, 2-[[6-deoxy-4-O-(4-O-methyl-∃-D-glycopyranosyl)-α-D-glucopyranosyl]-amino]-4-methoxy-1H-pyrrolo[2,3-d]pyrimidine-5-carbonitrile, 2-aminobutane, 2-bromo-2-(bromomethyl)-pentanedinitrile, 2-chloro-N-(2,3-dihydro-1,1,3-trimethyl-1H-inden-4-yl)-3-pyridinecarboxamide, 2-chloro-N-(2,6-dimethylphenyl)-N-(isothiocyanatomethyl)-acetamide, 2-phenylphenol (OPP), 3,4-dichloro-1-[4-(difluoromethoxy)phenyl]-1H-pyrrole-2,5-dione, 3,5-dichloro-N-[cyano-[(1-methyl-2-propynyl)-oxy]-methyl]-benzamide, 3-(1,1-dimethylpropyl-1-oxo-1H-indene-2-carbonitrile, 3-[2-(4-chlorophenyl)-5-ethoxy-3-isoxazolidinyl]-pyridine, 4-chloro-2-cyano-N,N-dimethyl-5-(4-methylphenyl)-1H-imidazole-1-sulphonamide, 4-methyl-tetrazolo[1,5-a]quinazolin-5-(4H)-one, 8-(1,1-dimethylethyl)-N-ethyl-N-propyl-1,4-dioxaspiro[4.5]decane-2-methanamine, 8-hydroxyquinoline sulphate, 9H-xanthene-2-[(phenylamino)-carbonyl]-9-carboxylic hydrazide, bis-(1-methylethyl)-3-methyl-4-[(3-methylbenzoyl)-oxy]-2,5-thiophenedicarboxylate, cis-1-(4-chlorophenyl)-2-(1H-1,2,4-triazol-1-yl)-cycloheptanol, cis-4-[3-[4-(1,1-dimethylpropyl)phenyl-2-methylpropyl]-2,6-dimethylmorpholinehydrochloride, ethyl [(4-chlorophenyl)-azo]-cyanoacetate, potassium hydrogen carbonate, methanetetrathiol sodium salt, methyl 1-(2,3-dihydro-2,2-dimethyl-1H-inden-1-yl)-1H-imidazole-5-carboxylate, methyl N-(2,6-dimethylphenyl)-N-(5-isoxazolylcarbonyl)-DL-alaninate, methyl N-(chloroacetyl)-N-(2,6-dimethylphenyl)-DL-alaninate, N-(2,3-dichloro-4-hydroxyphenyl)-1-methyl-cyclohexanecarboxamide, N-(2,6-dimethylphenyl)-2-methoxy-N-(tetrahydro-2-oxo-3-furanyl)-acetamide, N-(2,6-dimethylphenyl)-2-methoxy-N-(tetrahydro-2-oxo-3-thienyl)-acetamide, N-(2-chloro-4-nitrophenyl)-4-methyl-3-nitro-benzenesulphonamide, N-(4-cyclohexylphenyl)-1,4,5,6-tetrahydro-2-pyrimidineamine, N-(4-hexylphenyl)-1,4,5,6-tetrahydro-2-pyrimidineamine, N-(5-chloro-2-methylphenyl)-2-methoxy-N-(2-oxo-3-oxazolidinyl)-acetamide, N-(6-methoxy-3-pyridinyl)-cyclopropanecarboxarnide, N-[2,2,2-trichloro-1-[(chloroacetyl)-amino]-ethyl]-benzamide, N-[3-chloro-4,5-bis(2-propinyloxy)-phenyl]-N'-methoxy-methanimidamide, N-formyl-N-hydroxy-DL-alanine-sodium salt, O,O-diethyl [2-(dipropylamino)-2-oxoethyl]-ethylphosphoramidothioate, O-methyl S-phenyl phenylpropylphosphoramidothioate, S-methyl 1,2,3-benzothiadiazole-7-carbothioate, spiro[2H]-1-benzopyrane-2,1'-(3'H)-isobenzofuran]-3'-one, Bactericides:

bronopol, dichlorophen, nitrapyrin, nickel dimethyldithiocarbamate, kasugamycin, octhilinone, furancarboxylic acid, oxytetracyclin, probenazole, streptomycin, teclofialam, copper sulphate and other copper preparations.

Insecticides/acaricides/nematicides:
  abarnectin, acephate, acetamiprid, acrinathrin, alanycarb, aldicarb, aldoxycarb, alpha-cyperrnethrin, alphamethrin, amitraz, avermectin, AZ 60541, azadirachtin, azamethiphos, azinphos A, azinphos M, azocyclotin,
  *Bacillus popilliae, Bacillus sphaericus, Bacillus subtilis, Bacillus thuringiensis*, baculoviruses, *Beauveria bassiana, Beauveria tenella*, bendiocarb, benfuracarb, bensultap, benzoximate, betacyfluthrin, bifenazate, bifenthrin, bioethanomethrin, biopermethrin, BPMC, bromophos A, bufencarb, buprofezin, butathiofos, butocarboxim, butylpyridaben,
  cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, cis-resmethrin, cispermethirin, clocythrin, cloethocarb, clofentezine, cyanophos, cycloprene, cycloprothrin, cyfluthrin, cyhalothrin, cyhexatin, cypermethrin, cyromazine,
  deltamethrin, demeton M, demeton S, demeton-S-methyl, diafenthiuron, diazinon, dichlorvos, diflubenzuron, dimethoate, dimethylvinphos, diofenolan, disulfoton, docusatsodium, dofenapyn,
  eflusilanate, emamectin, empenthrin, endosulfan, Entomopfthora spp., esfenvalerate, ethiofencarb, ethion, ethoprophos, etofenprox, etoxazole, etrimfos,
  fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazinam, fluazuron, flubrocythrinate, flucycloxuron, flucythrinate, flufenoxuron, flutenzine, fluvalinate, fonophos, fosmethilan, fosthiazate, fubfenprox, furathiocarb,
  granulosis viruses,
  halofenozide, HCH, heptenophos, hexaflumuron, hexythiazox, hydroprene,
  imidacloprid, isazofos, isofenphos, isoxathion, ivermectin,
  lambda-cyhalothrin, lufenuron,
  malathion, mecarbam, metaldehyde, methamidophos, Metharhizium anisopliae, Metharhizium flavoviride, methidathion, methiocarb, methomyl, methoxyfenozide, metolcarb, metoxadiazone, mevinphos, milbemectin, monocrotophos,
  naled, nitenpyram, nithiazine, novaluron, nuclear polyhedrosis viruses,
  omethoat, oxamyl, oxydemethon M,
  Paecilomyces fumosoroseus, parathion A, parathion M, permethrin, phenthoat, phorat, phosalone, phosmet, phosphamidon, phoxim, pirimicarb, pirimiphos A, pirimiphos M, profenofos, promecarb, propoxur, prothiofos, prothoat, pymetrozine, pyraclofos, pyresmethrin, pyrethrum, pyridaben, pyridathion, pyrimidifen, pyriproxyfen,
  quinalphos,
  ribavirin,
  salithion, sebufos, silafluofen, spinosad, sulfotep, sulprofos,
  taufluvalinate, tebufenozide, tebufenpyrad, tebupirimiphos, teflubenzuron, tefluthrin, temephos, temivinphos, terbufos, tetrachlorvinphos, thetacypermethrin, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb,
  vamidothion, vaniliprole, Verticillium lecanii,
  YI 5302,
  zeta-cypermethrin, zolaprofos,
  (1R-cis)-[5-(phenylmethyl)-3-furanyl]-methyl-3-[(dihydro-2-oxo-3-(2H)-furanylidene)-methyl]-2,2-dimethylcyclopropanecarboxylate,
  (3-phenoxyphenyl)-methyl-2,2,3,3-tetramethylcyclopropanecarboxylate, 1-[(2-chloro-5-thiazolyl)methyl]tetrahydro-3,5-dimethyl-N-nitro-1,3,5-triazine-2-(1H)-imine,
  2-(2-chloro-6-fluorophenyl)-4-[4-(1,1-dimethylethyl)phenyl]-4,5-dihydro-oxazole,
  2-(acetlyoxy)-3-dodecyl-1,4-naphthalenedione,
  2-chloro-N-[[[4-(1-phenylethoxy)-phenyl]-amino]-carbonyl]-benzamide,
  2-chloro-N-[[[4-(2,2-dichloro-1,1-difluoroethoxy)-phenyl]-amino]-carbonyl]-benzamide,
  3-methylphenyl propylcarbamate
  4-[4-(4-ethoxyphenyl)-4-methylpentyl]-1-fluoro-2-phenoxy-benzene,
  4-chloro-2-(1,1-dimethylethyl)-5-[[2-(2,6-dimethyl-4-phenoxyphenoxy)ethyl]thio]-3-(2H)-pyridazinone,
  4-chloro-2-(2-chloro-2-methylpropyl)-5-[(6-iodo-3-pyridinyl)methoxy]-3(2H)-pyridazinone,
  4-chloro-5-[(6-chloro-3-pyridinyl)methoxy]-2-(3,4-dichlorophenyl)-3-(2H)-pyridazinone, Bacillus thuringiensis strain EG-2348,
  [2-benzoyl-1-(1,1-dimethylethyl)-hydrazinobenzoic acid,
  2,2-dimethyl-3-(2,4-dichlorophenyl)-2-oxo-1-oxaspiro[4.5]dec-3en-4-yl butanoate,
  [3-[(6-chloro-3-pyridinyl)methyl]-2-thiazolidinylidene]-cyanamide,
  dihydro-2-(nitromethylene)-2H-1,3-thiazine-3-(4H)-carboxaldehyde,
  ethyl [2-[[1,6-dihydro-6-oxo-1-(phenylmethyl)-4-pyridazinyl]-oxy]-ethyl]-carbamate,
  N-(3,4,4-trifluoro-1-oxo-3-butenyl)-glycine,
  N-(4-chlorophenyl)-3-[4-(difluoromethoxy)phenyl]-4,5-dihydro-4-phenyl-1H-pyrazole-1-carboxamide,
  N-[(2-chloro-5-thiazolyl)methyl]-N'-methyl-N''-nitroguanidine,
  N-methyl-N'-(1-methyl-2-propenyl)-1,2-hydrazinedicarbothioamide,
  N-methyl-N'-2-propenyl-1,2-hydrazinedicarbothioamide,
  O,O-diethyl [2-(dipropylamino)-2-oxoethyl]-ethylphosphoramidothioate.
Herbicides:
  acetochlor, acifluorfen(-sodium), aclonifen, alachlor, alloxydim(-sodium), ametryne, amidochlor, amidosulfuron, anilofos, asulam, atrazine, azafenidin, azimsulfuron, benazolin(-ethyl), benfuresate, bensulfuron(-methyl), bentazone, benzobicyclon, benzofenap, benzoylprop(-ethyl), bialaphos, bifenox, bispyribac(-sodium), bromobutide, bromofenoxim, bromoxynil, butachlor, butroxydim, butylate, cafenstrole, caloxydim, carbetamide, carfentrazone(-ethyl), chlomethoxyfen, chloramben, chloridazon, chlorimuron(-ethyl), chlornitrofen, chlorsulfuron, chlortoluron, cinidon(-ethyl), cinmethylin, cinosulfuron, clefoxydim, clethodim, clodinafop(-propargyl), clomazone, clomeprop, clopyralid, clopyrasulfuron(-methyl), cloransulam(-methyl), cumyluron, cyanazine, cybutryne, cycloate, cyclosulfamuron, cycloxydim, cyhalofop(-butyl), 2,4-D, 2,4-DB, 2,4-DP, desmedipham, diallate, dicamba, diclofop(-methyl), diclosulam, diethatyl(-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dyniron, epropodan, EPTC, esprocarb, ethalfluralin, ethametsulfuron(-methyl), ethofumesate, ethoxyfen, ethoxysulfuron, etobenzanid, enoxaprop(-P-ethyl), fentrazamide, flamprop(-isopropyl), flamprop(-isopropyl-L), flamprop(-methyl), flazasulfuron, florasulam, fluazifop(-P-butyl), fluazolate, flucarbazone, flufenacet, flumetsulam, flumiclorac(-pentyl), flumioxazin, flumipropyn, flumetsulam, fluometuron, fluorochloridone, fluoroglycofen(-ethyl), flupoxam, flupropacil, flurpyrsulfuiron(-methyl, -sodium), flurenol(-butyl), fluridone, fluroxypyr(-meptyl), flurprimidol, flurtamone, fluthiacet(-methyl), fluthiamide, fomesafen, glufosinate (-ammonium), glyphosate(-isopropylammonium), halosafen, haloxyfop(-ethoxyethyl), haloxyfop(-P-methyl), hexazinone, imazamethabenz(-methyl), imazamethapyr, imazamox, imazapic, imazapyr, imazaquin, imazethapyr, imazosulfuron, iodosulfuron(-methyl, -sodium), ioxynil, isopropalin, isoproturon, isouron, isoxaben, isoxachlortole, isoxaflutole, isoxapyrifop, lactofen, lenacil, linuron, MCPA, MCPP, mefenacet, mesotrione, metamitron, metazachlor, methabenzthiazuron, metobenzuron, metobromuron, (alpha-)metolachlor, metosulam, metoxuron, metribuzin, metsulfuron(-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pendralin, pentoxazone, phenmedipham, piperophos, pretilachlor, primisulfuron(-methyl), prometryn, propachlor, propanil, propaquizafop, propisochlor, propyzamide, prosulfocarb, prosuifiiron, pyraflufen(-ethyl), pyrazolate, pyrazosulfuron(-ethyl), pyrazoxyfen, pyribenzoxim, pyributicarb, pyridate, pyriminobac(-methyl), pyrithiobac(-sodium), quinchlorac, quinmerac, quinoclamine, quizalofop(-P-ethyl), quizalofop(-P-tefuryl), rimsulfuron, sethoxydim, simazine, simetryn, sulcotrione, sulfentrazone, sulfometuron(-methyl), sulfosate, sulfosulfuron, tebutam, tebuthiuron, tepraloxydim, terbuthylazine, terbutryn, thenylchlor, thiafluamide, thiazopyr, thidiazimin, thifensulfuron(-methyl), thiobencarb, tiocarbazil, tralkoxydim, triallate, triasulfuron, tribenuron(-methyl), triclopyr, tridiphane, trifluralin and triflusulfuron.

Furthermore, the active compound according to the invention, in its commercial formulations and in the use forms prepared from these formulations, can be present as a mixture with synergists. Synergists are compounds which increase the activity of the active compounds without it being necessary for the added synergist to be active itself.

The active compound content of the use forms prepared from the commercial formulations can vary within wide ranges. The concentration of active compound in the use forms can be from 0.0000001 to 95% by weight of active compound, preferably between 0.0001 and 1% by weight.

Application is carried out in a customary manner adapted to the use forms.

The active compounds are furthermore suitable for controlling animal pests, preferably arthropods and nematodes, in particular insects and arachnids, which are encountered in agriculture, in forestry, in the protection of stored products and of materials, and in the hygiene sector. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata.*

From the order of the Thysanura, for example, *Lepisma saccharina.*

From the order of the Collembola, for example, *Onychiurus amatus.*

From the order of the Blattaria or Orthoptera, for example, *Blatta orientalis, Periplaneta americana, Leucophaea maderae, Blattella germanica, Acheta domesticus,* Gryllotalpa spp., *Locusta migratoria* migratorioides, *Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Phylloxera vastatrix,* Pemphigus spp., *Pediculus humanus corporis,* Haematopinus spp. and Linognathus spp.

From the order of the Mallophaga, for example, Trichodectes spp. and Damalinea spp.

From the order of the Thysanoptera, for example, *Frankliniella occidentalis, Hercinothrips femoralis, Thrips palmi* and *Thrips tabaci.*

From the ordeer of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Phylloxera vasturix,* Pemphigus spp., *Macrosiphum avenae,* Myzus spp., *Phorodon humuli, Rhopalosiphum padi,* Empoasca spp., *Euscelis bilobatus, Nephotettix cincticeps, Lecanium comi, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Plutella xylostella, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana,* Cnaphalocerus spp. and *Aulema oryzae.*

From the order of the Coleoptera, for example, *Anobium punctatum, Rhizopertha dominica, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., Oryzaephilus surinamensis, Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis, Costelytra zealandica* and *Lissorhoptus oryzophilus.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Liriomyza spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae, Tipula paludosa,* Hylemnia spp. and Liviomyza spp.

From the order of the Siphonaptera, for example, *Xenopsylla cheopis* and Ceratophyllus spp.

From the order of the Arachnida, for example, *Scorpio maurus* and *Latrodectus mactans.*

From the order of the Acarina, for example, Acarus siro, Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp., Tetranychus spp., Hemitarsonemus spp. and Brevipulpus spp.

The phytoparasitic nematodes include, for example, Pratylenchus spp; *Radopholus similis, Ditylenchus dipsaci, Tylenchulus semi penetrans,* Heteroderma spp., Globodera spp., Meloidogyne spp., Aphelenchoides spp., Longidorus spp., Xiphinema spp., Trichodorus spp. and Bursaphelenchus spp.

The active compounds according to the invention have high insecticidal and acaricidal activity after foliar and soil application.

At certain concentrations or application rates, the compounds according to the invention also have fungicidal action. Furthermore, they can be used as microbicides or antimycotics.

When used against hygiene pests and pests of stored products, the active compound has excellent residual activity on wood and clay, and by good stability to alkali on limed substrates.

The active compounds according to the invention act not only against plant, hygiene and stored product pests, but also in the veterinary medicine sector against animal parasites (ectoparasites), such as hard ticks, soft ticks, mange mites, leaf mites, flies (biting and licking), parasitic fly larvae, lice, hair lice, feather lice and fleas. These parasites include:

From the order of the Anoplurida, for example, Haematopinus spp., Linognathus spp., Pediculus spp., Phtirus spp. and Solenopotes spp.

From the order of the Mallophagida and the suborders Amblycerina and Ischnocerina, for example, Trimenopon spp., Menopon spp., Trinoton spp., Bovicola spp., Werneckiella spp., Lepikentron spp., Damalina spp., Trichodectes spp. and Felicola spp.

From the order of the Diptera and the suborders Nematocerina and Brachycerina, for example, Aedes spp., Anopheles spp., Culex spp., Simulium spp., Eusimulium spp., Phlebotomus spp., Lutzomyia spp., Culicoides spp., Chrysops spp., Hybomitra spp., Atylotus spp., Tabanus spp., Haematopota spp., Philipomyia spp., Braula spp., Musca spp., Hydrotaea spp., Stomoxys spp., Haematobia spp., Morellia spp., Fannia spp., Glossina spp., Calliphora spp., Lucilia spp., Chrysomyia spp., Wohlfahrtia spp., Sarcophaga spp., Oestrus spp., Hypoderma spp., Gasterophilus spp., Hippobosca spp., Lipoptena spp. and Melophagus spp.

From the order of the Siphonapterida, for example Pulex spp., Ctenocephalides spp., Xenopsylla spp. and Ceratophyllus spp.

From the order of the Heteropterida, for example, Cimex spp., Triatoma spp., Rhodnius spp. and Panstrongylus spp.

From the order of the Blattarida, for example *Blatta orientalis, Periplaneta americana, Blattela germanica* and Supella spp.

From the subclass of the Acaria (Acarida) and the orders of the Meta- and Mesostigmata, for example, Argas spp., Omithodorus spp., Otobius spp., Ixodes spp., Amblyomma spp., Boophilus spp., Dermacentor spp., Haemophysalis spp., Hyalomma spp., Rhipicephalus spp., Dermanyssus spp., Raillietia spp., Pneumonyssus spp., Sternostoma spp. and Varroa spp.

From the order of the Actinedida (Prostigmata) und Acaridida (Astigmata), for example, Acarapis spp., Cheyletiella spp., Omithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Otodectes spp., Sarcoptes spp., Notoedres spp., Knemidocoptes spp., Cytodites spp. and Laminosioptes spp.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants by nasal administration, by dermal use in the form, for example, of dipping or bathing, spraying, pouring on and spotting on, washing and powdering, and also with the aid of molded articles containing the active compound, such as collars, ear marks, tail marks, limb bands, halters, marking devices and the like.

When used for cattle, poultry, pets and the like, the active compounds of the formula (I) can be used as formulations (for example powders, emulsions, free-flowing compositions), which comprise the active compounds in an amount of 1 to 80% by weight, directly or after 100 to 10,000-fold dilution, or they can be used as a chemical bath.

It has furthermore been found that the compounds of the formula (I) according to the invention also have a strong insecticidal action against insects which destroy industrial materials.

The following insects may be mentioned as examples and as preferred—but without a limitation:

Beetles, such as

*Hylotrupes bajulus, Chlorophorus pilosis, Anobium punctatum, Xestobium rufovillosum, Ptilinus pecticornis, Dendrobium pertinex, Emobius mollis, Priobium carpini, Lyctus brunneus, Lyctus africanus, Lyctus planicollis, Lyctus linearis, Lyctus pubescens, Trogoxylon aequale, Minthes rugicollis,* Xyleborus spec., Tryptodendron spec., *Apate monachus, Bostrychus capucins, Heterobostrychus brunneus,* Sinoxylon spec., *Dinoderus minutus.*

Hymenopterons, such as

*Sirex juvencus, Urocerus gigas, Urocerus gigas taignus, Urocerus augur*

Termites, such as

*Kalotermes flavicollis, Cryptotermes brevis, Heterotermes indicola, Reticulitermes flavipes, Reticulitermes santonensis, Reticulitermes lucifugus, Mastoternes darwiniensis, Zooternopsis nevadensis, Coptotermes formosanus.*

Bristletails, such as

*Lepisma saccarina.*

Industrial materials in the present connection are to be understood as meaning non-living materials, such as, preferably, plastics, adhesives, sizes, papers and cards, leather, wood and processed wood products and coating compositions.

Wood and processed wood products are materials to be protected, especially preferably, from insect infestation.

Wood and processed wood products which can be protected by the agents according to the invention or mixtures comprising these are to be understood as meaning, for example: building timber, wooden beams, railway sleepers, bridge components, boat jetties, wooden vehicles, boxes, pallets, containers, telegraph poles, wood panelling, wooden windows and doors, plywood, chipboard, joinery or wooden products which are used quite generally in house-building or in building joinery.

The active compounds can be used as such, in the form of concentrates or in generally customary formulations, such as powders, granules, solutions, suspensions, emulsions or pastes.

The formulations mentioned can be prepared in a manner known per se, for example by mixing the active compounds with at least one solvent or diluent, emulsifier, dispersing agent and/or binder or fixing agent, a water repellent, if appropriate siccatives and UV stabilizers and if appropriate dyestuffs and pigments, and also other processing auxiliaries.

The insecticidal compositions or concentrates used for the preservation of wood and timber products comprise the active compound according to the invention in a concentration of 0.0001 to 95% by weight, in particular 0.001 to 60% by weight.

The amount of the compositions or concentrates employed depends on the nature and occurrence of the insects and on the medium. The optimum amount employed can be determined for the use in each case by a series of tests. In general, however, it is sufficient to employ 0.0001 to 20% by weight, preferably 0.001 to 10% by weight, of the active compound, based on the material to be preserved.

Solvents and/or diluents which are used are an organochemical solvent or solvent mixture and/or an oily or oil-like organochemical solvent or solvent mixture of low volatility and/or a polar organochemical solvent or solvent mixture and/or water, and if appropriate an emulsifier and/or wetting agent.

Organochemical solvents which are preferably used are oily or oil-like solvents having an evaporation number above 35 and a flash point above 30° C., preferably above 45° C. Substances which are used as such oily or oil-like water-insoluble solvents of low volatility are appropriate mineral oils or aromatic fractions thereof, or solvent mixtures containing mineral oils, preferably white spirit, petroleum and/or alkylbenzene.

Mineral oils having a boiling range from 170 to 220° C., white spirit having a boiling range from 170 to 220° C., spindle oil having a boiling range from 250 to 350° C., petroleum and aromatics having a boiling range from 160 to 280° C., terpentine oil and the like, are advantageously employed.

In a preferred embodiment, liquid aliphatic hydrocarbons having a boiling range from 180 to 210° C. or highboiling mixtures of aromatic and aliphatic hydrocarbons having a boiling range from 180 to 220° C. and/or spindle oil and/or monochloronaphthalene, preferably α-monochloronaphthalene, are used.

The organic oily or oil-like solvents of low volatility which have an evaporation number above 35 and a flashpoint above 30° C., preferably above 45° C., can be replaced in part by organochemical solvents of high or medium volatility, providing that the solvent mixture likewise has an evaporation number above 35 and a flashpoint above 30° C., preferably above 45° C., and that the insecticide/fungicide mixture is soluble or emulsifiable in this solvent mixture.

According to a preferred embodiment, some of the organochemical solvent or solvent mixture is replaced by an aliphatic polar organochemical solvent or solvent mixture. Aliphatic organochemical solvents containing hydroxyl and/or ester and/or ether groups, such as, for example, glycol ethers, esters or the like, are preferably used.

Organochemical binders which are used in the context of the present invention are the synthetic resins and/or binding drying oils which are known per se, are water-dilutable and/or are soluble or dispersible or emulsifiable in the organochemical solvents employed, in particular binders consisting of or comprising an acrylate resin, a vinyl resin, for example polyvinyl acetate, polyester resin, polycondensation or polyaddition resin, polyurethane resin, alkyd resin or modified alkyd resin, phenolic resin, hydrocarbon resin, such as indenecumarone resin, silicone resin, drying vegetable oils and/or drying oils and/or physically drying binders based on a natural and/or synthetic resin.

The synthetic resin used as the binder can be employed in the form of an emulsion, dispersion or solution. Bitumen or bituminous substances can also be used as binders in an amount of up to 10% by weight. Dyestuffs, pigments, waterrepelling agents, odour correctants and inhibitors or anticorrosive agents and the like which are known per se can additionally be employed.

It is preferred according to the invention for the composition or concentrate to comprise, as the organochemical binder, at least one alkyd resin or modified alkyd resin and/or one drying vegetable oil. Alkyd resins having an oil content of more than 45% by weight, preferably 50 to 68% by weight, are preferably used according to the invention.

All or some of the binder mentioned can be replaced by a fixing agent (mixture) or a plasticizer (mixture). These additives are intended to prevent evaporation of the active compounds and crystallization or precipitation. They preferably replace 0.01 to 30% of the binder (based on 100% of the binder employed).

The plasticizers originate from the chemical classes of phthalic acid esters, such as dibutyl, dioctyl or benzyl butyl phthalate, phosphoric acid esters, such as tributyl phosphate, adipic acid esters, such as di-(2-ethylhexyl) adipate, stearates, such as butyl stearate or amyl stearate, oleates, such as butyl oleate, glycerol ethers or higher molecular weight glycol ethers, glycerol esters and p-toluenesulphonic acid esters.

Fixing agents are based chemically on polyvinyl alkyl ethers, such as, for example, polyvinyl methyl ether or ketones, such as benzophenone or ethylenebenzophenone.

Possible solvents or diluents are, in particular, also water, if appropriate as a mixture with one or more of the above-mentioned organochemical solvents or diluents, emulsifiers and dispersing agents.

Particularly effective preservation of wood is achieved by impregnation processes on a large industrial scale, for example vacuum, double vacuum or pressure processes.

The ready-to-use compositions can also comprise other insecticides, if appropriate, and also one or more fungicides, if appropriate.

Possible additional mixing components are, preferably, the insecticides and fungicides mentioned in WO 94/29268. The compounds mentioned in this document are an explicit constituent of the present application.

Especially preferred mixing partners which may be mentioned are insecticides, such as chlorpyriphos, phoxim, silafluofin, alphamethrin, cyfluthrin, cypermethrin, deltamethrin, permethrin, imidacloprid, NI-25, flufenoxuron, hexaflumuron and triflumuron, and also fungicides, such as epoxyconazole, hexaconazole, azaconazole, propiconazole, tebuconazole, cyproconazole, metconazole, imazalil, dichlorfluanid, tolylfluanid, 3-iodo-2-propinyl-butyl carbamate, N-octyl-isothiazolin-3-one and 4,5-dichloro-N-octylisothiazolin-3-one.

The active compounds according to the invention can be used particularly effectively for controlling plantdamaging insects, such as, for example, against the larvae of the mustard beetle (*Phaedon cochleariae*), against the larvae of the green rice leafhopper (*Nephotettix cincticeps*) and against the larvae of the green peach aphid (*Myzus persicae*).

In addition to the acaricidal, herbicidal and insecticidal properties described, a fungicidal activity of the active compounds according to the invention is noticeable. In both 'in vitro' and 'in vivo' studies, a broad fungicidal effect can be observed.

Moreover, it was noticed that the active compounds are, in particular, also suitable for controlling mildew, leaf blotch and Fusaria on the infected plants.

The preparation and the use of the active compounds according to the invention is shown in the Examples below.

PREPARATION EXAMPLES

Example 1

(Process A)             Comp. No. I-1-a-1

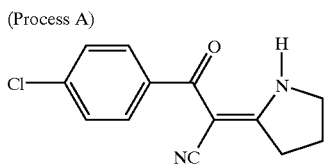

A mixture of 1.2 g of 2-ethoxy-pyrroline and 1 g of 4-chlorobenzoylacetonitrile in 20 ml of toluene is stirred at 100° C. for 1 hour. The resulting ethyl alcohol is distilled off azeotropically with toluene. After cooling to 20° C., the reaction mixture is crystallized by the addition of hexane and crystals are filtered off with suction.

This gives 1.1 g (yield: 74% of theory) of 3-(4-chlorophenyl)-3-oxo-2-pyrrolidin-2-ylidene-propionitrile of melting point 156–158° C.

Example 2

(Process E)             Comp. No. I-1-a-54

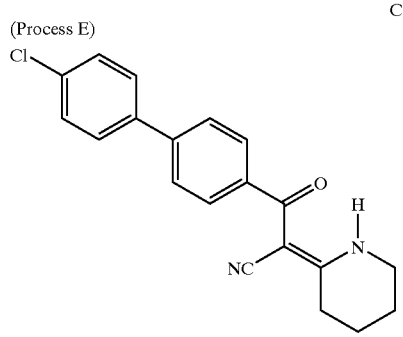

A solution of 1.85 g of 3-oxo-3-(4-bromophenyl)-2-piperidin-2-ylidene-propionitrile in 20 ml of dimethoxyethane, which was prepared at 20° C., is, under argon as protective gas, admixed with 1 g of 4-chlorophenylboronic acid and 360 mg of tetrakis(triphenylphosphine)-palladium, and the mixture is stirred at 20° C. for 15 minutes. 10 ml of 20% strength $Na_2CO_3$ solution are then added, and the mixture is heated at 80° C. for 24 h. The mixture is subsequently acidified with conc. hydrochloric acid, diluted with water and shaken with ethyl acetate, and the organic phase is separated off, washed with water, dried and filtered. The solvent is distilled off from the filtrate.

This gives 1.9 g (yield 95% of theory) of 3-(4'-chloro-biphenyl-4-yl)-3-oxo-2-piperidin-2-ylidene-propionitrile of melting point 134° C.

Example 3

(Process D)             Comp. No. I-1-b-1

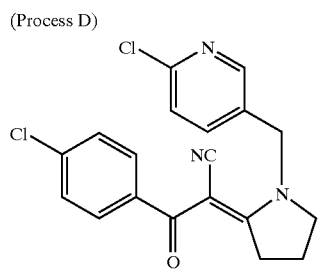

At 0° C., 1 g of the 3-(4-chlorophenyl)-3-oxo-2-pyrrolidin-2-ylidene-propionitrile prepared according to Example 1 is dissolved in 10 ml of THF and admixed with 0.16 g of NaH (60% pure), and the mixture is heated at 20° C. for four hours. 0.65 g of 2-chloro-5-chloromethyl-pyridine is then added, and the mixture is boiled under reflux for 4 hours. 100 mg of diazabicyclooctane (DABCO) are then added, and the mixture is heated under reflux for another 24 hours. The reaction mixture is then poured into ice-water, the solid residues are filtered off with suction, the liquid phase is shaken with ethyl acetate and the organic phase is then separated off, washed with water and filtered. The compounds contained in the solution were separated by column chromatography on a silica gel phase using the mobile phase hexane/acetone 7:3.

After evaporation of the solvent, one of the main fractions gave 0.65 g (yield 44% of theory) of 3-(4-chlorophenyl)-2-[1-(6-chloropyridin-3-yl-methyl)-pyrrolidin-2-yli-dene]-3-oxo-propionitrile of melting point 142–144° C.

Example 4

(Process D)     Comp. No. I-1-b-2

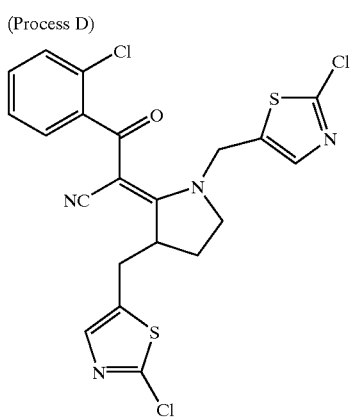

At 0° C., 1.5 g of 3-(2-chlorophenyl)-3-oxo-2-pyrrolidin-2-ylidene-propionitrile are dissolved in 10 ml of THF and admixed with 0.5 g of NaH (60% pure), and the mixture is heated at 20° C. for four hours. 1.1 g of 2-chloro-5-chloromethyl-thiazole in 10 ml of THF and 100 mg of diazabicyclooctane (DABCO) are then added, and the mixture is carefully maintained at room temperature (20° C.) and the progress of the reaction is monitored by thin-layer chromatography. The reaction mixture is then poured into ice-water, the solid residues are filtered off with suction, the liquid phase is shaken with ethyl acetate and the organic phase is then separated off, washed with water and filtered. The compounds contained in the solution were separated by column chromatography on a silica gel phase using the mobile phase n-hexane/acetone 7:3.

After evaporation of the solvent, one of the main fractions gave 0.4 g (yield 13% of theory) of 3-(2-chlorophenyl)-2-[3-(2-chloro-thiazol-5-yl)-1-(2-chloro-thiazol-5-yl-methyl)pyrrolidin-2-ylidene]-3-oxo-propionitrile.

Example 5

(Process D)     Comp. No. I-1-c-1

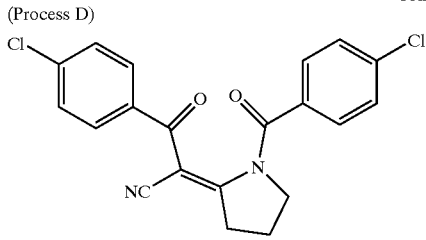

At 0° C., 1 g of the 3-(4-chlorophenyl)-3-oxo-2-pyrrolidin-2-ylidene-propionitrile prepared according to Example 1 is dissolved in 10 ml of THF and admixed with 0.3 g of NaH (60% pure), and the mixture is heated to 20° C. for two hours. 0.8 g of chlorobenzoyl chloride in 10 ml of THF is then added, and the mixture is stirred at room temperature for another 24 hours. The reaction mixture is then poured into ice-water and extracted with ethyl acetate, the extract is dried over magnesium sulphate and the solvent is evaporated under reduced pressure. The residue was chromatographed over silica gel using n-hexane/acetone 7:3. After evaporation of the solvent, one of the main fractions gave 0.2 g (yield 14% of theory) of 2-[1-(4-chlorobenzoyl)pyrrolidin-2-ylidene]-3-(4-chlorophenyl)-3-oxo-propionitrile of melting point 218° C.

Example 6

(Process A)     Comp. No. I-1-d-1

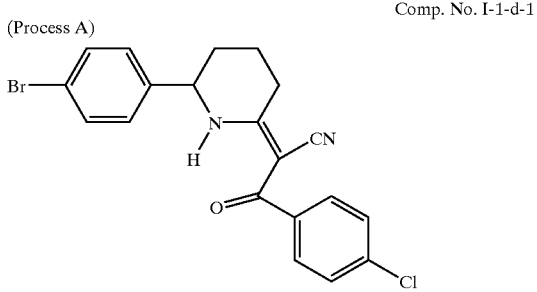

A mixture of 0.9 g of 6-(4-bromophenyl)-2-ethoxy-tetrahydropyridine and 0.5 g of chlorobenzoylacetonitrile in 10 ml of toluene is heated to 120° C. and kept at this temperature for two hours. The reaction products contained in the solution are separated by column chromatography on a silica gel phase using the mobile phase methylene chloride/ethyl acetate 5:3.

After evaporation of the solvent, the main fraction gave 0.9 g (yield 77.6% of theory) of 2-[6-(4-bromo-phenyl)-piperidin-2-ylidene]-3-(4-chloro-phenyl)-3-oxo-propionitrile.

Example 7

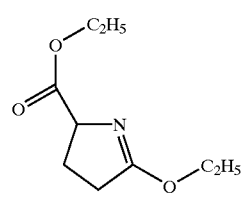

(Intermediates for process A according to formula (III); Comp. No. III-1)

63 g of ethyl DL-pyroglutamate in 200 ml of methylene chloride are added dropwise over a period of 10 minutes to a solution of 500 ml of triethyloxonium tetrafluoroboronate (Meerwein salt, as a one molar solution in methylene chloride), and the mixture is heated under reflux for 24 hours. The solution is then cooled to 0° C. and carefully admixed with 63 g of sodium carbonate in 300 ml of water. The reactino product is extracted with methylene chloride, the organic phase is dried and filtered and the solvent is subsequently stripped off under waterpump vacuum.

This gives 12.5 g (yield 12.9% of theory) of ethyl 5-ethoxy-3,4-dihydro-2H-pyrrole-2-carboxylate.

(Process A)

Comp. No. I-1-d-2

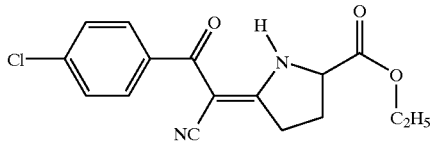

A mixture of 6.1 g of the ethyl 5-ethoxy-3,4-dihydro-2H-pyrrole-2-carboxylate prepared and 6 g of chlorobenzoylacetonitrile in 50 ml of toluene is stirred at 100° C. for 1 hour. The resulting ethyl alcohol is subsequently distilled off azeotropically together with the toluene. After cooling to 20° C., the reaction product is crystallized by addition of hexane and filtered off with suction. The main product is separated by column chromatography on a silica gel phase using n-hexane/acetone 7:3.

After evaporation of the solvent, the main fraction gave 6.9 g (yield 67% of theory) of ethyl 5-[2-(4-chloro-phenyl)-1-cyano-2-oxo-ethylidene]-pyrrolidine-2-carboxylate of melting point 108–110° C.

Example 8

Comp.No. I-1-d-3

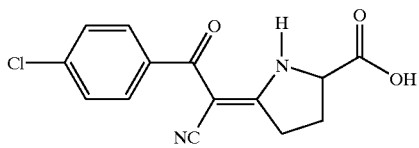

4.8 g of the ethyl 5-[2-(4-chloro-phenyl)-1-cyano-2-oxo-ethylidene]-pyrrolidine-2-carboxylate prepared according to Example 7 are, at 40° C., dissolved in 30 ml of ethanol and admixed with 10 ml of 20% strength NaOH. The mixture is stirred at the stated temperature for one hour and then concentrated under waterpump vacuum and adjusted to pH 1–2 using HCl.

2.5 g of 5-[2-(4-chloro-phenyl)-1-cyano-2-oxo-ethylidene]-pyrrolidine-2-carboxylic acid of melting point 134–136° C. are obtained as residue.

Example 9

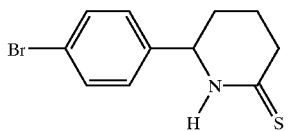

(Intermediate for compounds of the formula (III) according to formula (V); Comp. No. V-1)

38.5 g of 6-(4-bromo-phenyl)-piperidin-2-one and 31 g of [2,4-bis(4-methoxyphenyl)-1,3,2,4-dithiadiphosphetane-2,4-disulphide] (Lawesson's reagent) in 200 ml of anhydrous toluene are heated at reflux for about 2 hours. The progress of the reaction is monitored by thin-layer chromatography. The reaction products contained in the solution are separated by column chromatography on a silica gel phase using the mobile phase methylene chloride/ethyl acetate 5:3.

After evaporation of the solvent, the main fraction gave 20 g (yield 50% of theory) of 6-(4-bromo-phenyl)-piperidine-2-thione of melting point 157° C.

After evaporation of the solvent, the main fraction gave 20 g (yield 50% of theory) of 6-(4-bromo-phenyl)-piperidine-2-thione.

Comp. No. III-2

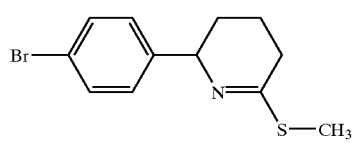

(Intermediate for process A according to formula (III))

At 20° C., 8 g of 6-(4-bromo-phenyl)-piperidine-2-thione are dissolved in 150 ml of acetone and admixed successively with 10 g of potassium carbonate and 10 g of methyl iodide. Over a period of 24 hours, during which the mixture is heated at reflux, the progress of the reaction is monitored by thin-layer chromatography. After cooling, the solid is filtered off with suction and the filtrate is concentrated. The reaction products contained in the solution are separated by column chromatography on a silica gel phase using the mobile phase methylene chloride/ethyl acetate 5:3.

After evaporation of the solvent, the main fraction gave 2.1 g (yield 25% of theory) of 6-(4-bromo-phenyl)-2methylmercapto-2,3,4,5-tetrahydropyridine as a yellow oil.

Example 10

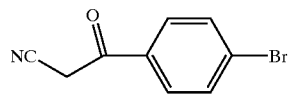

(Intermediate for process A according to formula (II); Comp. No. II-1)

80 g of ethyl 4-bromobenzoate are initially charged in 2000 ml of dioxane and 50 g of acetonitrile. After addition of 3 drops of tris[2-(2-methoxyethoxy)-ethyl]-amine (TDA-1), the mixture is heated to 90° C. Subsequently, 70 g of potassium tert-butoxide are added a little at a time, and the mixture is heated at reflux for three hours. The mixture is then concentrated under waterpump vacuum, the residue is taken up in water, acidified using 10% strength HCl, admixed with methylene chloride and filtered, the methylene chloride phase is extracted with saturated sodium carbonate solution and the dried organic phase is concentrated to dryness.

82 g (yield 72% of theory) of 3-(4-bromo-phenyl)-3-oxo-propionitrile are obtained as residue.

Example 11

Comp. No. XI-1

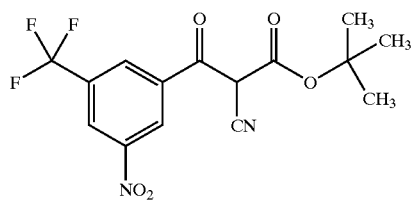

Under protective gas (argon), 5.84 g of NaH (60% pure) are initially charged in 147 ml of toluene. At 20° C., 10.51 g of tertbutyl cyanoacetate (98% pure) in 9 ml of toluene are then added dropwise, and the mixture is stirred at room temperature for 45 minutes. 18.5 g of 3-nitro-5-trifluoromethyl-benzoyl chloride in 9 ml of toluene are then added dropwise, and the mixture is stirred for another 24 hours. 168 ml of water are then added carefully, and the toluene phase is separated off and washed with about 190 ml of water. The combined aqueous phases are washed twice with methylene chloride, acidified with 2 N HCl and then again extracted twice with methylene chloride. The combined organic phases are washed with water, dried over Na$_2$SO$_4$ and concentrated under waterpump vacuum.

13.1 g (yield 53% of theory) of tert-butyl 2-cyano-3-(3-nitro-5-trifluoromethyl-phenyl)-3-oxo-propionate are obtained as residue.

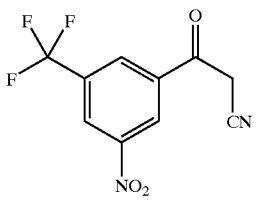

(Intermediate for process A according to formula (II); Comp. No. II-2)

13 g of tert-butyl 2-cyano-3-(3-nitro-5-trifluoromethyl-phenyl)-3-oxo-propionate are then initially charged in 55 ml of toluene and, at 20° C., admixed with 0.07 g of p-toluenesulphonic acid (monohydrate). The mixture is heated under reflux for two hours and the progress of the reaction is monitored by thin-layer chromatography. The solution is subsequently concentrated, and the residue is taken up in methylene chloride/methanol (99:1) and then filtered through silica gel, and the solvent is stripped off.

This gives 5.5 g (yield 59% of theory) of 3-(3-nitro-5-trifluoro-phenyl)-3-oxo-propionitrile.

Example 12

(Process C)

Comp. No. I-1-a-110

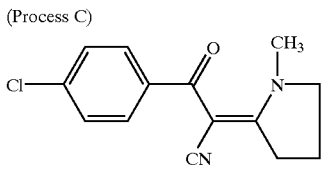

3.06 g (20 mmol) of 1-methyl-2-chloro-2-pyrroline-iminium chloride are suspended in 10 ml of toluene. Under protective gas, 1.79 g (19 mmol) of 4-chlorobenzoyl-acetonitrile (as a solution in 30 ml of chloroform) and then 3.06 ml (22 mmol) of triethylamine (as a solution in 30 ml of chloroform) are added dropwise, in each case at 0° C. The addition is carried out with effective cooling. After one hour of stirring at 0° C. and 2 hours of stirring at room temperature, another 3.06 g of 1-methyl-2-chloro-2-pyrroline-iminium chloride and 4.18 ml of triethylamine are added at 0° C.

The mixture is stirred at room temperature for 48 hours. The reaction mixture is subsequently poured into 30 ml of ice-water and extracted three times with in each case 50 ml of chloroform. The chloroform phase is dried over magnesium sulphate and then concentrated to dryness.

The resulting reaction product is separated by column chromatography on a silica gel phase using the mobile phase hexane/ethyl acetate 1:1.

After evaporation of the solvent, the main fraction gave 620 mg (yield 24% of theory) of 3-(4-chloro-phenyl)-3-oxo-2-(1-methyl-pyrrolidin-2-ylidene)-propionitrile of melting point 115° C.

Example 13

(Process K)

Comp. No. I-1-a-151

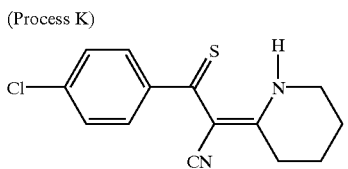

1 g of the compound from Example I-1-a-55 are dissolved in 10 ml of toluene, and the mixture is admixed with 1.58 g (3.9 mmol) of Lawesson's reagent and heated to reflux. After 1 hour, it was no longer possible to detect starting material by thin-layer chromatography using the mobile phase hexane/ethyl aceetate. Half of the solvent was then stripped off and the precipitated crystals were filtered off with suction. The product which precipitates out after further concentration is separated by column chromatography on a silica gel phase using the mobile phase hexane/ethyl acetate.

After evaporation of the solvent, the main fraction gave 0.560 g (yield 53% of theory) of 3-(4-chloro-phenyl)-3-thio-2-piperidin-2-ylidene-propionitrile of melting point 137° C.

Example 14

Comp. No. I-1-a-150

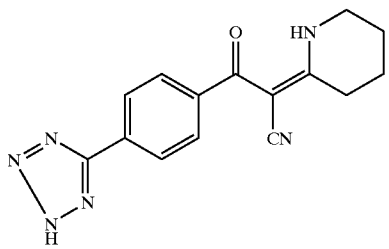

257 g (1.02 mmol) of the compound from Example No. I-1-a-62 together with 246 mg (1.2 mmol) of trimethyltin azide in toluene are heated under reflux for 24 hours. After 24 hours, a further 120 mg of tin azide are added and the mixture is once more heated under reflux for 5 hours. The tin adduct is subsequently filtered off with suction. The starting material separates off on addition of 5 ml of 2 N NaOH solution, and is filtered off with suction. The pH is adjusted to pH=1 using 2 N HCl and the prepared product is filtered off with suction from the mixture which had been cooled to 0° C.

This gave 0.06 g (yield 18% of theory) of solid 3-(4tetrazolyl-phenyl)-3-oxo-2-piperidin-2-ylidene-propionitrile of melting point greater than 220° C.

Example 15

Comp. No. I-1-a-137

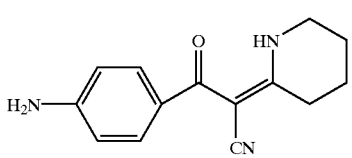

2.33 g (8.6 mmol) of the compound from Example No. I-1-a-63 are dissolved in 100 ml of ethanol (p.a.), and 300 mg of Raney® nickel are added to the solution. Nitrogen is passed into the reaction mixture for 5 minutes, followed by hydrogen at atmospheric pressure for 8 hours. The mixture is subsequently again flushed with nitrogen for 5 minutes. The Raney® nickel is filtered off, and rinsed with 20 ml of ethanol and 50 ml of dichloromethane. The combined filtrates are evaporated to dryness, and the residue is dried under high vacuum.

This gave 2.03 g (yield 97.8% of theory) of solid 3-(4-nitrophenyl)-3-oxo-2-piperidin-2-ylidene-propionitrile of melting point 182° C.

Example 16

Comp. No. I-1-a-138

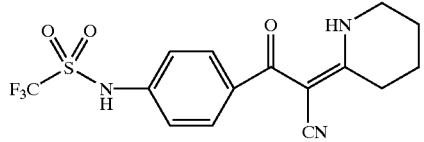

Under protective gas, 0.4 g (1.66 mmol) of the compound from Example No. I-1-a-137 in 5 ml of dichloromethane are initially charged into an apparatus freed from moisture by heating, and the mixture is cooled to 20° C. At this temperature, 0.28 ml (2.0 mmol) of triethylamine are added, and 0.33 ml (1.98 mmol) of trifluoromethanesulphonic anhydride are then added dropwise. The mixture is stirred at −20° C. for 15 minutes. After warming to 0° C., stirring is continued for another 2 hours. To bring the reaction to completion, a further 0.33 mmol of trifluoromethanesulphonic anhydride are added at −20° C. After warming to 0° C., the mixture is stirred for another hour.

The reaction mixture is diluted with 50 ml of dichloromethane and poured into 20 ml of 0° C.-cold 1 N HCl. The organic phase is separated off, dried over magnesium sulphate and concentrated using a rotary evaporator. The reaction products are separated by column chromatography on a silica phase using the mobile phase ethyl acetate/cyclohexane 1:1.

This gives 316 mg (yield 51% of theory) of 3-[4-(trifluoromethanesulphonylamino)-phenyl]-3-oxo-2-piperidin-2-ylidene-propionitrile of melting point 197° C.

Example 17

Comp. N. I-2-a-6

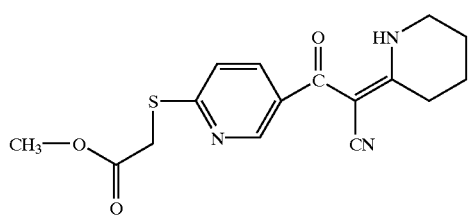

1.5 g (5,73 mmol) of the compound from Example No. I-2-a-2, 0.91 g (8.6 mmol) of methyl thioglycolate and 0.91 g of sodium carbonate in 10 ml of anhydrous acetone are heated to 80° C. After 2 hours, a further 8.6 mmol of the methyl thioglycolate and 8.6 mmol of sodium methoxide are added, and the mixture is heated under reflux for 24 hours. After cooling to room temperature, the reaction mixture is poured into 150 ml of 1 M HCl. The reaction product is filtered off as a solid residue and washed repeatedly with 10 ml of methyl tert-butyl ether.

This gives 1.350 g of 3-[(2-methoxycarbonylmethylthio)-pyrid-5-yl]-3-oxo-2-piperidin]-2-ylidene-propionitrile (yield 71% of theory) of melting point 146° C.

Example 18

Comp. No. I-2-a-7

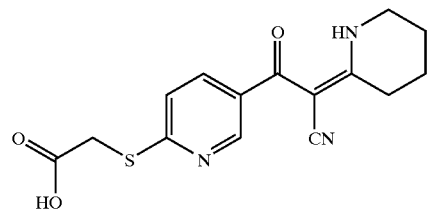

At 0° C., 700 mg (2.1 mmol) of the compound from Example No. I-2-a-6 are initially charged in 1.1 ml of a 1:1 mixture of 2 N NaOH and methanol. The mixture is subsequently stirred at 0° C. for 1 hour and at room temperature for a further 4 hours.

The resulting reaction solution is adjusted to pH 6 using 6 N HCl. The precipitated product is freed from moisture by pressing on clay and dried under high vacuum.

This gives 551 mg (yield: 82.7% of theory) of 3-[4-(mercaptoacetic acid)-pyridyl]-3-oxo-2-pyridinyl-2-ylidene-propionitrile of melting point 155° C.

Analogously to the Preparation Examples 1 and 2, and in accordance with the general statements about the preparation of compounds of the formula (I-1-a), the following compounds are obtained:

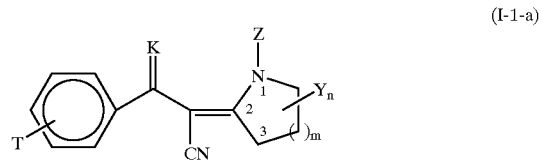

(I-1-a)

TABLE 1

| Comp. No. | K | T | $Y_n$ | Z | m | M.p. °C. |
|---|---|---|---|---|---|---|
| I-1-a-2 | O | 4-OCH$_3$ | — | H | 1 | 145 |
| I-1-a-3 | O | 3,5-Cl$_2$ | — | H | 1 | 124 |
| I-1-a-4 | O | 4-t-C$_4$H$_9$ | — | H | 1 | 204–205 |

TABLE 1-continued

| Comp. No. | K | T | $Y_n$ | Z | m | M.p. ° C. |
|---|---|---|---|---|---|---|
| I-1-a-5 | O | 4-CH$_3$ | — | H | 1 | 166–168 |
| I-1-a-6 | O | 2,6-Cl$_2$ | — | H | 1 | 196–198 |
| I-1-a-7 | O | 2,4-Cl$_2$ | — | H | 1 | 120 |
| I-1-a-8 | O | 3,4-Cl$_2$ | — | H | 1 | 179–180 |
| I-1-a-9 | O | 2,5-Cl$_2$ | — | H | 1 | 152 |
| I-1-a-10 | O | 4-O—C$_6$H$_5$ | — | H | 1 | 136–138 |
| I-1-a-11 | O | 4-CF$_3$ | — | H | 1 | 138–140 |
| I-1-a-12 | O | 4-OCF$_3$ | — | H | 1 | 98 |
| I-1-a-13 | O | 4-Br | — | H | 1 | 192 |
| I-1-a-14 | O | 3,5-(CF$_3$)$_2$ | — | H | 1 | 78 |
| I-1-a-15 | O | 3-O—C$_6$H$_5$ | — | H | 1 | 178 |
| I-1-a-16 | O | 2-NO$_2$ | — | H | 1 | 206 |
| I-1-a-17 | O | 3-NO$_2$ | — | H | 1 | 223 |
| I-1-a-18 | O | 3-Cl, 4-F | — | H | 1 | 176 |
| I-1-a-19 | O | 4-Cl, 3-F | — | H | 1 | 178 |
| I-1-a-20 | O | 4-CN | — | H | 1 | 215 |
| I-1-a-21 | O | 4-NO$_2$ | — | H | 1 | 221 |
| I-1-a-22 | O | 3-Br | — | H | 1 | 193 |
| I-1-a-23 | O | 2-S-CHF$_2$ | — | H | 1 | 206 |
| I-1-a-24 | O | 2,4-Cl$_2$, 5-F | — | H | 1 | 175 |
| I-1-a-25 | O | 3-CF$_3$ | — | H | 1 | 119 |
| I-1-a-26 | O | 3-Cl | — | H | 1 | 178 |
| I-1-a-27 | Q | 3,5-Cl$_2$, 4-F | — | H | 1 | 203 |
| I-1-a-28 | O | 4-Cl, 2-F | — | H | 1 | 182 |
| I-1-a-29 | O | 3-CF$_3$, 5-CH$_3$ | — | H | 1 | 143 |
| I-1-a-30 | O | 3-Cl, 4,5-F$_2$ | — | H | 1 | 160 |
| I-1-a-31 | O | 2-F | — | H | 1 | 168 |
| I-1-a-32 | O | 3-F | — | H | 1 | 167 |
| I-1-a-33 | O | 4-Cl, 3-CF$_3$ | — | H | 1 | 156 |
| I-1-a-34 | O | 4-CN, 2,5-F$_2$ | — | H | 1 | 206 |
| I-1-a-35 | O | 2,3-F$_2$ | — | H | 1 | 185 |
| I-1-a-36 | O | 4-CF$_3$, 3-F | — | H | 1 | 185 |
| I-1-a-37 | O | 3,4-O—CF$_2$—O— | — | H | 1 | 159 |
| I-1-a-38 | O | 3,5-(CH$_3$)$_2$ | — | H | 1 | 165 |
| I-1-a-39 | O | 3,4,5-(OCH$_3$)$_3$ | — | H | 1 | 159 |
| I-1-a-40 | O | 2-Br, 4-OCH$_3$ | — | H | 1 | 216 |
| I-1-a-41 | O | 4-(4'-Cl—C$_6$H$_4$)— | — | H | 1 | 131 |
| I-1-a-42 | O | 2,4-Cl$_2$ | — | H | 2 | 100 |
| I-1-a-43 | O | 4-t-C$_4$H$_9$ | — | H | 2 | 169–170 |
| I-1-a-44 | O | 4-CH$_3$ | — | H | 2 | 165 |
| I-1-a-45 | O | 3,4-Cl$_2$ | — | H | 2 | 135 |
| I-1-a-46 | O | 2,5-Cl$_2$ | — | H | 2 | 102 |
| I-1-a-47 | O | 4-OCH$_3$ | — | H | 2 | 104 |
| I-1-a-48 | O | 3,5-Cl$_2$ | — | H | 2 | 90–92 |
| I-1-a-49 | O | 2,6-Cl$_2$ | — | H | 2 | 176–178 |
| I-1-a-50 | O | 4-O—C$_6$H$_5$ | — | H | 2 | 128–130 |
| I-1-a-51 | O | 4-CF$_3$ | — | H | 2 | 126–128 |
| I-1-a-52 | Q | 4-OCF$_3$ | — | H | 2 | 82–84 |
| I-1-a-53 | O | 4-Br | — | H | 2 | 149 |
| 1-1-a-54 | O | 4-(4'-Cl—C$_6$H$_4$) | — | H | 2 | 134 |
| I-1-a-55 | O | 4-Cl | — | H | 2 | 149 |
| I-1-a-56 | O | 3,5-(CF$_3$)$_2$ | — | H | 2 | 64 |
| I-1-a-57 | O | 2-NO$_2$ | — | H | 2 | 222 |
| I-1-a-58 | O | 3-O—C$_6$H$_5$ | — | H | 2 | Öl |
| I-1-a-59 | O | 3-NO$_2$ | — | H | 2 | 194 |
| I-1-a-60 | O | 3-Cl, 4-F | — | H | 2 | 148 |
| I-1-a-61 | O | 4-Cl, 3-F | — | H | 2 | 167 |
| 1-I-a-62 | O | 4-CN | — | H | 2 | 196 |
| I-1-a-63 | O | 4-NO$_2$ | — | H | 2 | 217 |
| I-1-a-64 | O | 3-Br | — | H | 2 | 107 |
| I-1-a-65 | O | 2-S—CHF$_2$ | — | H | 2 | 130 |
| I-1-a-66 | O | 2,4-Cl$_2$, 5-F | — | H | 2 | 132 |
| I-1-a-67 | O | 3-CF$_3$ | — | H | 2 | 129 |
| I-1-a-68 | O | 3-Cl | — | H | 2 | 123 |
| I-1-a-69 | O | 3-C$_6$H$_5$ | — | H | 2 | 188 |
| I-1-a-70 | O | 3-(3'-Cl, 4'-F—C$_6$H$_3$)— | — | H | 2 | 216 |
| I-1-a-71 | O | 3-(4'-F—C$_6$H$_4$)— | — | H | 2 | 234 |
| I-1-a-72 | O | 3-(3'-NO$_2$—C$_6$H$_4$)— | — | H | 2 | 157 |
| I-1-a-73 | O | 3,5-Cl$_2$, 4-F | — | H | 2 | 150 |
| I-1-a-74 | O | 4-Cl, 2-F | — | H | 2 | 177 |
| I-1-a-75 | O | 3-CF$_3$, 5-CH$_3$ | — | H | 2 | 114 |
| I-1-a-76 | O | 3-Cl, 4,5-F$_2$ | — | H | 2 | 140 |
| I-1-a-77 | O | 2-F | — | H | 2 | 154 |
| I-1-a-78 | O | 3-F | — | H | 2 | 145 |
| I-1-a-79 | O | 4-Cl, 3-CF$_3$ | — | H | 2 | 141 |
| I-1-a-80 | O | 4-CN, 2,5-F$_2$ | — | H | 2 | 187 |
| I-1-a-81 | O | 2,3-F$_2$ | — | H | 2 | 210 |

TABLE 1-continued

| Comp. No. | K | T | $Y_n$ | Z | m | M.p. ° C. |
|---|---|---|---|---|---|---|
| I-1-a-82 | O | 4-$CF_3$, 3-F | — | H | 2 | 160 |
| I-1-a-83 | O | 3,4-O—$CF_2$—O— | — | H | 2 | 163 |
| I-1-a-84 | O | 3,5-$Br_2$ | — | H | 2 | 118 |
| I-1-a-85 | O | 3,5-$(CH_3)_2$ | — | H | 2 | 133 |
| I-1-a-86 | O | 3,4,5-$(OCH_3)_3$ | — | H | 2 | 139 |
| I-1-a-87 | O | 3,5-$(OC_2H_5)_2$ | — | H | 2 | 105 |
| I-1-a-88 | O | 3-Br, 4-$OCH_3$ | — | H | 2 | 171 |
| I-1-a-89 | O | 4-Cl | — | H | 3 | 158 |
| I-1-a-90 | O | 4-$CH_3$ | — | H | 3 | 124 |
| I-1-a-91 | O | 4-$OCH_3$ | — | H | 3 | 82 |
| I-1-a-92 | O | 3-Cl | — | H | 3 | 136 |
| I-1-a-93 | O | 2,4-$Cl_2$ | — | H | 3 | 167 |
| I-1-a-94 | O | 3,5-$(CF_3)_2$ | — | H | 3 | 129 |
| I-1-a-95 | O | 3-Br | — | H | 3 | 137 |
| I-1-a-96 | O | 3-$NO_2$ | — | H | 3 | 127 |
| I-1-a-97 | O | 3-O—$C_6H_5$ | — | H | 3 | 103 |
| I-1-a-98 | O | 3-$CF_3$ | — | H | 3 | 145 |
| I-1-a-99 | O | 4-Cl, 3-F | — | H | 3 | 143 |
| I-1-a-100 | O | 3-Cl, 4-F | — | H | 3 | 145 |
| I-1-a-101 | O | 3-Cl | — | H | 3 | 139 |
| I-1-a-102 | O | 4-CN, 2,5-$F_2$ | — | H | 3 | 192 |
| I-1-a-103 | O | 2,4,5-$F_3$ | — | H | 1 | 174 |
| I-1-a-104 | O | 3-$NO_2$, 5-$CF_3$ | — | H | 1 | 152 |
| I-1-a-105 | O | 4-Cl, 2,5-$F_2$ | — | H | 1 | 162 |
| I-1-a-106 | O | 3,4,5-$(OC_2H_5)_3$ | — | H | 1 | 166 |
| I-1-a-107 | O | 2,4-$F_2$ | — | H | 1 | 180 |
| I-1-a-108 | O | 4-$CO_2CH_3$ | — | H | 1 | 207 |
| I-1-a-109 | O | 4-$CO_2H$ | — | H | 1 | >220 |
| I-1-a-110 | O | 4-Cl | — | $CH_3$ | 1 | 115 |
| I-1-a-111 | O | 2,5-$F_2$, 4-CN | — | $CH_3$ | 1 | 158 |
| I-1-a-112 | O | 2-F, 4-Br | — | H | 1 | 195 |
| I-1-a-113 | O | 2,6-$Cl_2$, 4-$CF_3$ | — | H | 1 | 114 |
| I-1-a-114 | O | 2-F, 4-$NO_2$ | — | H | I | 176 |
| I-1-a-115 | O | 2-F, 4-$CF_3$ | — | H | 1 | 169 |
| I-1-a-116 | O | 2-$CF_3$ | — | H | 1 | 148 |
| I-1-a-117 | O | 3,4-O—$(CF_2)_2$—O— | — | H | 1 | 109 |
| I-1-a-118 | O | 2,3-O—$CF_2$—O— | — | H | 1 | 147 |
| I-1-a-119 | O | 2-Cl, 4-$SCH_3$ | — | H | 1 | 174 |
| I-1-a-120 | O | 2,4-$Cl_2$, 5-$NO_2$ | — | H | 1 | 190 |
| I-1-a-121 | O | 2,6-$F_2$ | — | H | 1 | 184 |
| I-1-a-122 | O | 2-Cl, 3-$CF_3$ | — | H | 1 | 206 |
| I-1-a-123 | O | 4-$OCF_3$, 3-$NO_2$ | — | H | 1 | 113 |
| I-1-a-124 | O | 2-$NO_2$, 4-Cl | — | H | 1 | 184 |
| 1-1-a-125 | O | 4-Cl | 3,3-$(CH_3)_2$ | H | 1 | 141 |
| I-1-a-126 | O | 4-Cl | 5,6-CH=CH—CH=CH— | H | 2 | 196 |
| I-1-a-127 | O | 2,5-$F_2$, 4-CN | 5,6-CH=CH—CH=CH— | H | 2 | 215 |
| I-1-a-128 | O | 3,5-$(CF_3)_2$ | 5,6-CH=CH—CH=CH— | H | 2 | 167 |
| I-1-a-129 | O | 2,4,5-$F_3$ | — | H | 2 | 189 |
| I-1-a-130 | O | 3-$NO_2$, 5-$CF_3$ | — | H | 2 | 138 |
| I-1-a-131 | O | 4-Cl, 2,5-$F_2$ | — | H | 2 | 186 |
| I-1-a-132 | O | 3,4,5-$(OC_2H_5)_3$ | — | H | 2 | 155 |
| I-1-a-133 | O | 2,4-$F_2$ | — | H | 2 | 168 |
| I-1-a-134 | O | 4-$CO_2CH_3$ | — | H | 2 | 179 |
| I-1-a-135 | O | 4-$CO_2H$ | — | H | 2 | >220 |
| I-1-a-136 | O | 4-Br, 2-F | — | H | 2 | 175 |
| I-1-a-137 | O | 4-$NH_2$ | — | H | 2 | 182 |
| I-1-a-138 | O | 4-NH$SO_2CF_3$ | — | H | 2 | 197 |
| I-1-a-139 | O | 2-$CF_3$ | — | H | 2 | 153 |
| I-1-a-140 | O | 2,6-$Cl_2$, 4-$CF_3$ | — | H | 2 | 164 |
| I-1-a-141 | O | 2-F, 4-$NO_2$ | — | H | 2 | 192 |
| I-1-a-142 | O | 2-F, 4-$CF_3$ | — | H | 2 | 180 |
| I-1-a-143 | O | 4-$SCH_3$, 2-Cl | — | H | 2 | 128 |
| I-1-a-144 | O | 2,4-$Cl_2$, 5-$NO_2$ | — | H | 2 | 204 |
| I-1-a-145 | O | 4-Cl, 2-F, 5-$NO_2$ | — | H | 2 | 177 |
| I-1-a-146 | O | 4-$OCF_3$, 3-$NO_2$ | — | H | 2 | 113 |
| I-1-a-147 | O | 4-$OCF_3$, 3-$NH_2$ | — | H | 2 | 141 |
| I-1-a-148 | O | 4-Br, 2-F, 5-$NH_2$ | — | H | 2 | 148 |
| I-1-a-149 | O | 4-Cl | — | $CH_3$ | 2 | 110 |
| I-1-a-150 | O | 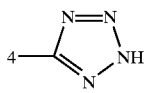 | — | H | 2 | >220 |

TABLE 1-continued

| Comp. No. | K | T | $Y_n$ | Z | m | M.p. °C. |
|---|---|---|---|---|---|---|
| I-1-a-151 | S | 4-Cl | — | H | 2 | 137 |
| I-1-a-152 | O | 4-(2-CH'$_3$—C$_6$H$_4$) | — | H | 2 | 199 |
| I-1-a-153 | O | 4-(3,5-(CF$_3$)'—C$_6$H$_3$) | — | H | 2 | 220 |
| I-1-a-154 | O | 4-NHSO$_2$—CH$_3$ | — | H | 2 | 210 |
| I-1-a-155 | O | 2,5-F$_2$, 4-(tetrazolyl) | — | H | 2 | >220 |
| I-1-a-156 | O | 2,4-F$_2$, 5-NO$_2$ | — | H | 2 | 207 |
| I-1-a-157 | O | 2,6-F$_2$ | — | H | 2 | 195 |
| I-1-a-158 | O | 2-F, 3-CF$_3$ | — | H | 2 | 189 |
| I-1-a-159 | O | 2-Cl, 6-F | — | H | 2 | |
| 1-1-a-160 | O | 2-Cl, 3-CF$_3$ | — | H | 2 | 171 |
| I-1-a-161 | S | 4-Cl | — | CH$_3$ | 1 | 172 |
| I-1-a-162 | O | 3-O-(3-Cl'-C$_6$H$_4$), 5-NO$_2$ | — | H | 1 | 161 |
| I-1-a-163 | O | 3-O-(3-Cl'-C$_6$H$_4$), 5-NO$_2$ | — | H | 2 | 94 |

Analogously to Preparation Example 1, and in accordance with the general statements about the preparation, the following compounds of the formula I-2-a are obtained:

TABLE 2

(I-2-a)

| Comp. No. | T | $Y_n$ | m | M.p. °C. |
|---|---|---|---|---|
| I-2-a-1 | 2-Cl | — | 1 | 156–158 |
| I-2-a-2 | 2-Cl | — | 2 | 258–260 |
| I-2-a-3 | 2,6-Cl$_2$, 4-CH$_3$ | — | 1 | >220 |
| I-2-a-4 | 6-Cl | — | 1 | 30 |
| I-2-a-5 | 2-Cl | 5,6-CH=CH—CH=CH— | 2 | 183 |
| I-2-a-6 | 2-S—CH$_2$—CO$_2$—CH$_3$ | — | 2 | 146 |
| I-2-a-7 | 2-S—CH$_2$—CO$_2$—H | — | 2 | 155 |
| I-2-a-8 | 2,6-Cl$_2$ | — | 2 | 121 |
| I-2-a-9 | 2,6-Cl$_2$, 4-CH$_3$ | — | 2 | 176 |
| I-2-a-10 | 2-S-4-[(4'-C$_6$H$_5$)—C$_6$H$_4$] | — | 2 | 197 |
| I-2-a-11 | 6-Cl | — | 2 | 179 |

Analogously to Preparation Example 1, and in accordance with the general statements about the preparation, the following compounds of the formula I-3-a are obtained:

TABLE 3

(I-3-a)

| Comp. N. | T | m | M.p. °C. |
|---|---|---|---|
| I-3-a-1 | 2-Br | 1 | 201 |
| I-3-a-2 | 3-Br | 1 | 198 |
| I-3-a-3 | 2-Cl | 2 | 141 |
| I-3-a-4 | 2-Br | 2 | 159 |
| I-3-a-5 | 3-Br | 2 | 215 |
| I-3-a-6 | 3-Br | 3 | 162 |
| I-3-a-7 | 2-Cl | 3 | 176 |
| I-3-a-8 | 2-Br | 3 | 163 |
| I-3-a-9 | 3-(4-Cl'—C$_6$H$_4$), 2-CF$_3$ | 1 | 176 |
| I-3-a-10 | 2,3-(CH=CH—CCl=CH)— | 1 | 198 |
| I-3-a-11 | 2-(4-Cl'—C$_6$H$_4$) | 2 | 207 |
| I-3-a-12 | 3-(4-Cl'-C$_6$H$_4$), 2-CF$_3$ | 2 | 170 |
| I-3-a-13 | 2-(3-Cl', 4-F'—C$_6$H$_3$) | 2 | 175 |
| I-3-a-14 | 2-(3,5-(CF$_3$)'$_2$—C$_6$H$_3$) | 2 | >223 |

TABLE 3-continued

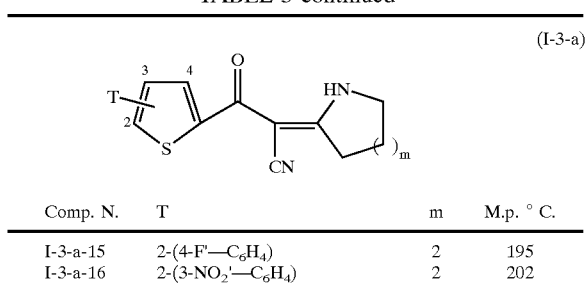
(I-3-a)

| Comp. N. | T | m | M.p. °C. |
|---|---|---|---|
| I-3-a-15 | 2-(4-F'—$C_6H_4$) | 2 | 195 |
| I-3-a-16 | 2-(3-$NO_2$'—$C_6H_4$) | 2 | 202 |

Analogously to Preparation Example 1, and in accordance with the general statements about the preparation, the following compounds of the formula I-4-a are obtained:

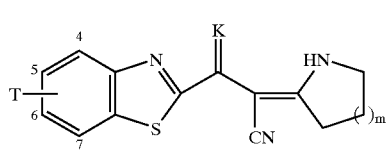
(I-4-a)

TABLE 4

| Comp. No. | K | T | $Y_n$ | m | M.p. °C. |
|---|---|---|---|---|---|
| I-4-a-1 | O | 7-Cl | — | 1 | >220 |
| I-4-a-2 | O | 7-Cl | — | 2 | >220 |

Analogously to Preparation Example 1, and in accordance with the general statements about the preparation, the following compounds of the formula I-5-a are obtained:

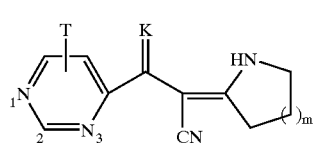
(I-5-a)

TABLE 5

| Comp.No. | K | T | $Y_n$ | m | M.p. °C. |
|---|---|---|---|---|---|
| I-5-a-1 | O | 2-$SCH_3$, 5-Br | — | 1 | 170 |
| I-5-a-2 | O | 2-$SCH_3$, 5-Br | — | 2 | 180 |

Analogously to Preparation Example 1, and in accordance with the general statements about the preparation, the following compounds of the formula I-6-a are obtained:

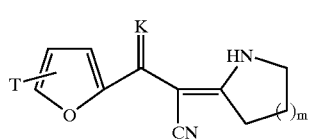
(I-6-a)

TABLE 6

| Comp. No. | K | T | $Y_n$ | m | M.p. °C. |
|---|---|---|---|---|---|
| I-6-a-1 | O | H | — | 1 | 199 |
| I-6-a-2 | O | H | — | 2 | |

Analogously to Preparation Example 3, and in accordance with the general statements about the preparation, the following compounds of the formula I-1-b are obtained:

TABLE 7

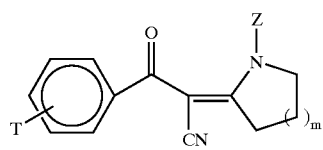
(I-1-b)

| Comp. No. | T | m | Z | M.p. °C. |
|---|---|---|---|---|
| I-1-b-3 | 4-Cl | 1 | 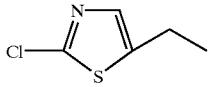 | 118–120 |
| I-1-b-4 | 3,4-$Cl_2$ | 1 |  | 68–70 |
| I-1-b-5 | 4-Cl | 2 |  | 136–138 |
| I-1-b-6 | 2-Cl | 2 |  | 204–205 |
| I-1-b-7 | 2-Cl | 1 | 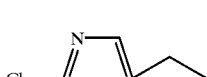 | 100–101 |

Analogously to Preparation Example 7, the compound I-1-d-4 of m.p. 222–224° C. is obtained.

Comp. No. I-1-d-4
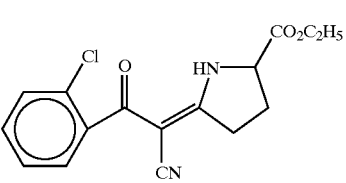

Analogously to Preparation Example 3, the compound I-1-d-5 of m.p. 130–132° C. is obtained.

Comp. No. I-1-d-5
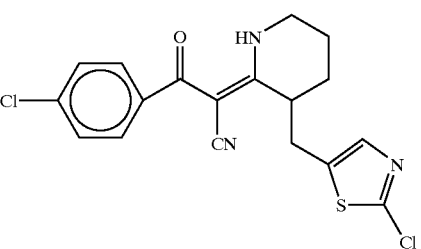

Example

Phaedon Larvae Test

Solvent: 7 parts by weight of dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

Cabbage leaves (Brassica oleracea) are treated by being dipped into the preparation of active compound of the desired concentration and are populated with larvae of the mustard beetle (Phaedon cochleariae) while the leaves are still moist.

After the desired period of time, the kill in % is determined. 100% means that all beetle larvae have been killed; 0% means that none of the beetle larvae have been killed.

In this test, for example, the following compounds of the Preparation Examples show good activity: I-1-a-11, I-1-a-12, I-1-a-52.

Example

Spodoptera frugiperda Test

Solvent: 7 parts by weight of dimethylformamide
Emulsifier:: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

Cabbage leaves (Brassica oleracea) are treated by being dipped into the preparation of active compound of the desired concentration and are populated with caterpillars of the army worm (Spodoptera frugiperda) while the leaves are still moist.

After the desired period of time, the kill in % is determined. 100% means that all caterpillars have been killed; 0% means that none of the caterpillars have been killed.

In this test, for example, the following compounds of the Preparation Examples show good activity: I-2-a-2, compound according to Preparation Example 3.

Example

Tetranychus Test (OP-resistant/Dip Treatment)

Solvent: 7 parts by weight of dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

Bean plants (Phaseolus vulgaris) which are heavily infested by all stages of the greenhouse red spider mite (Tetranychus urticae) are dipped into the preparation of active compound of the desired concentration.

After the desired period of time, the kill in % is determined. 100% means that all spider mites have been killed; 0% means that none of the spider mites have been killed.

In this test, for example, the following compounds of the Preparation Examples show good activity: I-1-a-7, I-1-a-48, I-1-a-56.

Example

Post Emergence Test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5 to 15 cm are sprayed with the preparation of active compound such that the particular desired amounts of active compound are applied per unit area. After 3 weeks, the degree of damage to the plants is assessed in % damage in comparison to the development of the untreated controls.

The figures denote:

| | | |
|---|---|---|
| 0% | = | no effect (like untreated control) |
| 100% | = | total destruction |

In this test, for example, the compounds of Preparation Example I-1-a-9, I-1-a-14, I-1-a-20, I-1-a-54, I-1-a-55, I-1-a-62, I-2-a-2 show strong activity against weeds, and some of them are tolerated well by crop plants, such as, for example, wheat.

Example

Pre-emergence Test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of active compound. The amount of water per unit area is advantageously kept constant. The concentration of active compound in the preparation is immaterial, only the active compound application rate per unit area matters. After three weeks, the degree of damage to the plants is assessed in % damage in comparison with the development of the untreated control.

The figures denote:

| | | |
|---|---|---|
| 0% | = | no effect (like untreated control) |
| 100% | = | total destruction |

In this test, for example, the compounds of Preparation Example I-1-a-14, I-1-a-46, I-1-a-51, I-1-a-52, I-1-a-53, I-1-a-54, I-1-a-55, I-1-a-62, I-1-a-66, I-2-a-2 show strong activity against weeds, and some of them are tolerated well by crop plants, such as, for example, wheat and soya.

What is claimed is:

1. A compound of the formula (I)

(I)

wherein
  Ar represents $Ar^1$, wherein $Ar^1$ is selected from the group consisting of
    i) phenyl being substituted with from one to five substituents, ii) naphthyl being substituted with from one to five substituents, and
iii) mono- or bicyclic hetaryl having five to ten ring atoms and being substituted with from zero to five substituents,
with said substituents being selected from the group consisting of
halogen, $C_1$–$C_8$-alkyl, $C_2$–$C_8$-alkenyl, $C_2$–$C_8$-alkinyl, $C_1$–$C_8$-alkoxy, $C_2$–$C_8$-alkenyloxy, $C_3$–$C_8$-alkinyloxy, $C_1$–$C_8$-alkylthio, $C_1$–$C_6$-alkylsulfinyl, $C_1$–$C_6$-alkylsulfonyl, $C_1$–$C_6$-halogenoalkyl, $C_1$–$C_6$-halogeno-alkoxy, $C_2$–$C_8$-halogeno-alkenyloxy, $C_1$–$C_2$-alkylidenediyl-dioxy, $C_1$–$C_2$-halogeno-alkylidenediyl-dioxy, halogeno-$C_1$–$C_4$-alkylthio, halogeno-$C_1$–$C_4$-alkylsulfinyl, halogeno-$C_1$–$C_4$-alkylsulfonyl, hydroxyl, mercapto, nitro, cyano, amino, a) —L—CO—$R^7$,

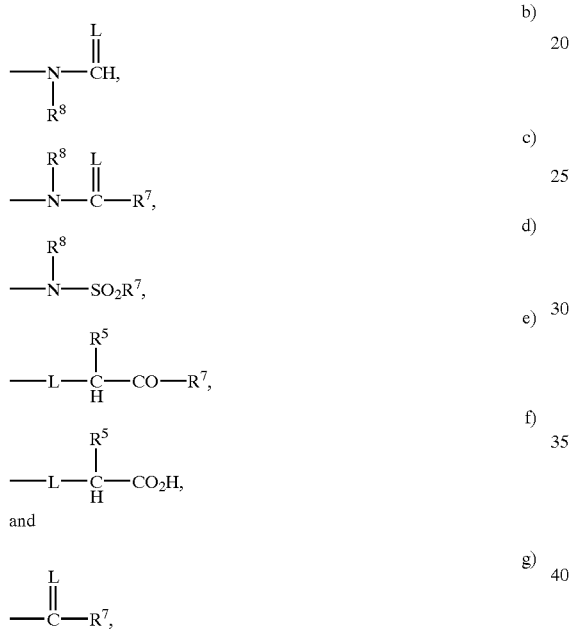

or Ar represents $Ar^2$, where $Ar^2$ represents $Ar^1$ which is additionally substituted by phenyl, naphthyl, five- or six-membered hetaryl, phenyl-$C_1$–$C_4$-alkyl, phenoxy, phenyl-S(O)$_g$—, five- or six-membered hetaryloxy or hetaryl-S(O)$_g$, where these substituents for their part are in each case unsubstituted or mono- to tetrasubstituted by halogen, $C_1$–$C_6$-alkyl, $C_1$–$C_6$-alkoxy, $C_1$–$C_4$-halogenoalkyl, $C_1$–$C_4$-halogenoalkoxy, nitro or cyano, and K represents oxygen or sulphur,
L represents oxygen or sulphur,
X represents CN,

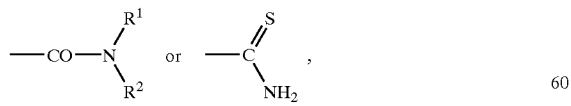

Y represents halogen, $C_1$–$C_6$-alkyl, $C_1$–$C_4$-halogenoalkyl, $C_1$–$C_6$-alkoxy, or represents phenyl, phenyl-$C_1$–$C_4$-alkyl, five- or six-membered hetaryl or five- or six-membered hetaryl-$C_1$–$C_4$-alkyl, each of which is unsubstituted or mono- to tetrasubstituted by halogen, $C_1$–$C_6$-alkyl, $C_1$–$C_6$-alkoxy, $C_1$–$C_4$-halogenoalkyl, $C_1$–$C_4$-halogenoalkoxy, cyano or nitro, or represents the groups

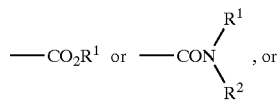

two adjacent $Y_n$ represent a 5- to 8-membered, saturated or unsaturated cycle which may be interrupted by 1 to 3 heteroatoms from the group consisting of N, O, S and which may be unsubstituted or mono- to tri-substituted by halogen, $C_1$–$C_4$-alkyl, $C_1$–$C_4$-alkoxy, $C_1$–$C_4$-halogenoalkyl, $C_1$–$C_4$-halogenoalkoxy, cyano or nitro, and Z represents hydrogen, or represents in each case unsubstituted or fluorine- and/or chlorine-substituted $C_1$–$C_8$-alkyl, cyano-$C_1$–$C_6$-alkyl, $C_3$–$C_8$-alkenyl, $C_3$–$C_8$-alkinyl, $C_3$–$C_8$-cycloalkyl, $C_3$–$C_8$-cycloalkyl-$C_1$–$C_2$-alkyl, $C_1$–$C_4$-alkoxy-$C_1$–$C_4$-alkyl, $C_1$–$C_4$-halogenoalkoxy-$C_1$–$C_4$-alkyl, or represents phenoxy-$C_1$–$C_4$-alkyl, phenyl-$C_1$–$C_4$-alkyloxy-$C_1$–$C_4$-alkyl, phenylthio-$C_1$–$C_4$-alkyl, phenyl-$C_1$–$C_4$-alkylthio-$C_1$–$C_4$-alkyl, phenyl, phenyl-$C_1$–$C_4$-alkyl, five- or six-membered hetaryl, five- or six-membered hetaryl-$C_1$–$C_4$-alkyl, each of which is unsubstituted or mono- to tetrasubstituted by halogen, $C_1$–$C_6$-alkyl, $C_1$–$C_6$-alkoxy, $C_1$–$C_4$-halogenoalkyl, $C_1$–$C_4$-halogenoalkoxy, nitro or cyano, or represents the groups

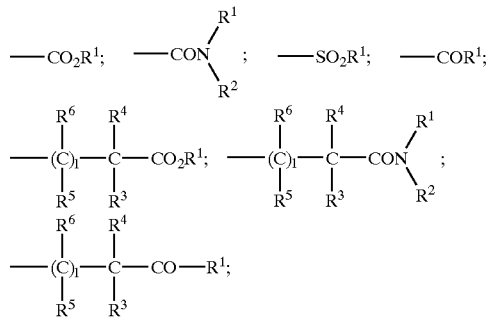

or cyano,
g represents 0 to 2,
I represents 0 to 2,
$R^1$ represents hydrogen (but not for the radicals —CO$_2$$R^1$ and —SO$_2$$R^1$), or represents in each case fluorine- and/or chlorine-substituted $C_1$–$C_{10}$-alkyl, $C_2$–$C_{10}$-alkenyl, $C_3$–$C_6$-alkinyl, or represents in each case unsubstituted or fluorine-, chlorine-, $C_1$–$C_4$-alkyl-, $C_1$–$C_4$-alkoxy-substituted $C_3$–$C_8$-cycloalkyl or $C_5$–$C_8$-cycloalkenyl wherein optionally one methylene group may be interrupted by oxygen or sulphur, or represents phenyl, pyridyl, thienyl, pyrimidyl, thiazolyl, phenyl-$C_1$–$C_4$-alkyl, pyridyl-$C_1$–$C_2$-alkyl, thiazolyl-$C_1$–$C_2$-alkyl, each of which is unsubstituted or mono- to tetrasubstituted by halogen, $C_1$–$C_6$-alkyl, $C_1$–$C_6$-alkoxy, $C_1$–$C_4$-halogenoalkyl, $C_1$–$C_4$-halogenoalkoxy, cyano or nitro,
$R^2$ represents hydrogen, or represents in each case unsubstituted or fluorine- and/or chlorine-substituted $C_1$–$C_6$-alkyl, $C_3$–$C_6$-alkenyl, $C_3$–$C_6$-alkinyl, $C_1$–$C_6$-alkoxy, $C_3$–$C_6$-alkenyloxy or represents phenyl, phenyl-$C_1$–$C_4$-alkyl or phenyl-$C_1$–$C_4$-alkoxy, each of which is unsubstituted or mono- to tetrasubstituted by halogen, $C_1$–$C_6$-alkyl, $C_1$–$C_6$-alkoxy, $C_1$–$C_4$-halogenoalkyl, $C_1$–$C_4$-halogenoalkoxy, cyano or nitro, or $R^1$, $R^2$ together with the nitrogen atom to which they are attached represent an unsubstituted or $C_1$–$C_4$-alkyl-substituted five- to eight-membered cycle wherein optionally one methylene group may be replaced by oxygen or sulphur, $R^3$ represents hydrogen, or unsubstituted or halogen-substituted $C_1$–$C_6$-alkyl or represents phenyl or phenyl-$C_1$–$C_2$-alkyl each of which is unsubstituted or mono- to tetrasubstituted by halogen, $C_1$–$C_6$-alkyl, $C_1$–$C_6$-alkoxy, $C_1$–$C_4$-halogenoalkyl, $C_1$–$C_4$-halogenoalkoxy, cyano or nitro, $R^4$ represents hydrogen or $C_1$–$C_6$-alkyl, $R^5$, $R^6$ independently of one another each represent hydrogen or unsubstituted or fluorine- and/or chlorine-substituted $C_1$–$C_4$-alkyl, $R^7$ represents in each case unsubstituted or fluorine- and/or chlorine-substituted $C_1$–$C_{10}$-alkyl, $C_2$–$C_{10}$-alkenyl, $C_3$–$C_{10}$-alkinyl, $C_1$–$C_{10}$-alkoxy, $C_1$–$C_4$-alkoxy-$C_1$–$C_4$-alkyl, $C_1$–$C_4$-alkylthio-$C_1$–$C_4$-alkyl, in each case unsubstituted or fluorine- and/or chlorine-, $C_1$–$C_4$-alkyl-, $C_1$–$C_4$-alkoxy-substituted $C_3$–$C_8$-cycloalkyl or $C_3$–$C_8$-cycloalkyloxy wherein optionally one methylene group may be replaced by oxygen or sulphur, or represents phenyl, phenoxy, benzyloxy, five- or six-membered hetaryl or phenyl-$C_1$–$C_4$-alkyl, each of which is unsubstituted or mono- to tetra-substituted by halogen, $C_1$–$C_6$-alkyl, $C_1$–$C_6$-alkoxy, $C_1$–$C_4$-halogeno-alkyl, $C_1$–$C_4$-halogenoalkoxy, cyano or nitro, or, in the case of the radicals a) and c) mentioned under Ar, also represents a group $$-N\begin{matrix}R^9\\R^{10}\end{matrix}$$

for the radical g), also represents hydroxyl, $R^8$ represents hydrogen or $C_1$–$C_4$-alkyl, $R^9$ represents hydrogen, or represents unsubstituted or fluorine- and/or chlorine-substituted $C_1$–$C_{10}$-alkyl, $C_3$–$C_8$-alkenyl, $C_3$–$C_8$-alkinyl, $C_1$–$C_{10}$-alkoxy, $C_3$–$C_8$-alkenyloxy, unsubstituted or fluorine-, chlorine-, $C_1$–$C_4$-alkyl- or $C_1$–$C_4$-alkoxy-substituted $C_3$–$C_8$-cycloalkyl wherein optionally one methylene group may be replaced by oxygen or sulphur, or represents phenyl, phenyl-$C_1$–$C_4$-alkyl or phenyl-$C_1$–$C_2$-alkoxy, each of which is unsubstituted or mono- to tetrasubstituted by halogen, $C_1$–$C_6$-alkyl, $C_1$–$C_6$-alkoxy, $C_1$–$C_4$-halogenoalkyl, $C_1$–$C_4$-halogenoalkoxy, cyano or nitro, $R^{10}$ represents hydrogen, $C_1$–$C_6$-alkyl or $C_3$–$C_6$-alkenyl, or $R^9$, $R^{10}$ together with the nitrogen atom to which they are attached represent an unsubstituted or $C_1$–$C_4$-alkyl-substituted five- to eight-membered cycle wherein optionally one methylene group may be replaced by oxygen or sulphur, and m represents 1 to 3, and n depending on m, represents 0 to 3, except for compounds of the following formula $m = 1, 2, 3.$ 2. A compound according to claim 1, wherein K represents oxygen or sulphur, Ar represents $Ar^1$, $Ar^1$ is selected from the group consisting of
 i) phenyl being substituted with from one to three substituents,
 ii) naphthyl being substituted with from one to three substituents, and
 iii) quinolinyl, thienyl, pyrimidyl, furanyl, thiazolyl, benzothiazolyl, oxazolyl, pyrazolyl or pyridyl mono- or bicyclic each of which may be substituted with from zero to three substituents, with said substituents being selected from the group consisting of
 fluorine, chlorine, bromine, $C_1$–$C_6$-alkyl, $C_2$–$C_6$-alkenyl, $C_2$–$C_6$-alkinyl, $C_1$–$C_6$-alkoxy, $C_3$–$C_6$-alkenyloxy, $C_3$–$C_6$-alkinyloxy, $C_1$–$C_6$-alkylthio, $C_1$–$C_4$-alkylsulfinyl, $C_1$–$C_4$-alkylsulfonyl, $C_1$–$C_4$-halogenoalkyl, $C_1$–$C_4$-halogeno-alkoxy, $C_2$–$C_4$-halo-genoalkenyloxy, $C_1$–$C_2$-alkylidenediyl-dioxy, $C_1$–$C_2$-halogenoalkylidenediyl-dioxy, halogeno-$C_1$–$C_2$-alkylthio, halogeno-$C_1$–$C_2$-alkylsulfinyl, halogeno-$C_1$–$C_2$-alkylsulfonyl, hydroxyl, mercapto, nitro, cyano, amino, a) —L—CO—$R^7$, b) $-N(R^8)-C(=L)H$, c) $-N(H)-C(=L)-R^7$, d) $NHSO_2R^7$, e) $-L-C(R^5)(H)-CO-R^7$, f) $-L-C(R^5)(H)-CO_2H$, and g) $-C(=L)-R^7$, or Ar represents $Ar^2$ where $Ar^2$ represents $Ar^1$ which is additionally substituted by phenyl, pyridyl, pyrimidyl, thienyl, furanyl, thiazolyl, tetrazolyl, triazolyl, benzyl, phenoxy, phenyl-S(O)$_g$—, pyridyloxy, pyrimidyloxy, thiazolyloxy, pyridyl-S(O)$_g$—, pyrimidyl-S(O)$_g$— or thiazolyl-S(O)$_g$—, where these substituents are unsubstituted or mono- to tri-substituted by fluorine, chlorine, bromine, $C_1$–$C_4$-alkyl, $C_2$–$C_4$-alkenyl, $C_1$–$C_4$-alkoxy, $C_1$–$C_2$-halogenoalkyl, $C_1$–$C_2$-halogenoalkoxy, nitro or cyano, where g represents 0 to 2, and L represents oxygen or sulphur, X represents CN,

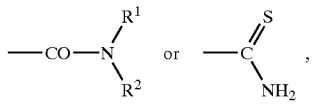

Y represents fluorine, $C_1$–$C_4$-alkyl, $C_1$–$C_2$-halogenoalkyl, $C_1$–$C_4$-alkoxy, or represents phenyl, phenyl-$C_1$–$C_2$-alkyl, thiazolylmethyl, pyridylmethyl, each of which is unsubstituted or mono- to tri-substituted by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, cyano or nitro, or represents the groups

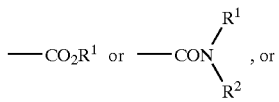

two adjacent $Y_n$ furthermore represent a 5- to 6-membered, saturated or unsaturated cycle which may be interrupted by a heteroatom from the group consisting of N, O, S and which may be unsubstituted or mono- to disubstituted by fluorine, chlorine, bromine, methyl, t-butyl, methoxy, trifluoromethyl, trifluoromethoxy, cyano or nitro, and Z represents hydrogen, or represents in each case unsubstituted or fluorine- and/or chlorine-substituted $C_1$–$C_6$-alkyl, cyano-$C_1$–$C_3$-alkyl, $C_3$–$C_6$-alkenyl, $C_3$–$C_8$-alkinyl, $C_3$–$C_6$-cycloalkyl, $C_3$–$C_6$-cycloalkyl-$C_1$–$C_2$-alkyl, $C_1$–$C_4$-alkoxy-$C_1$–$C_2$-alkyl, $C_1$–$C_4$-halogeno-$C_1$–$C_2$-alkyl, or represents phenoxy-$C_1$–$C_2$-alkyl, phenyl-$C_1$–$C_2$-alkyloxy-$C_1$–$C_2$-alkyl, phenylthio-$C_1$–$C_2$-alkyl, phenyl-$C_1$–$C_2$-alkylthio-$C_1$–$C_2$-alkyl, phenyl-$C_1$–$C_2$-alkyl, phenyl, pyridyl-$C_1$–$C_2$-alkyl, thiazolyl-$C_1$–$C_2$-alkyl, each of which is unsubstituted or mono- to tri-substituted by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, nitro or cyano, or represents the groups

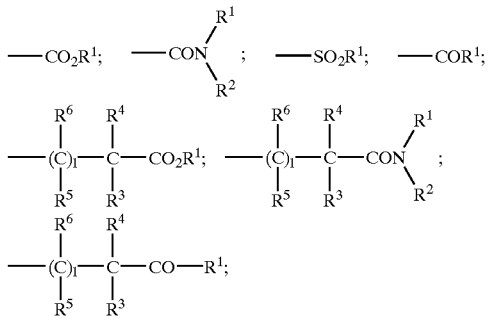

or cyano,

I represents 0 to 1, $R^1$ represents hydrogen (but not for the radicals —$CO_2R^1$ and —$SO_2R^1$), or represents in each case unsubstituted or fluorine- and/or chlorine-substituted $C_1$–$C_6$-alkyl, $C_2$–$C_6$-alkenyl, $C_3$–$C_4$-alkinyl, or represents unsubstituted or fluorine-, chlorine-, $C_1$–$C_2$-alkyl, $C_1$–$C_2$-alkoxy-substituted $C_3$–$C_6$-cycloalkyl or represents phenyl or benzyl, each of which is unsubstituted or mono- to disubstituted by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, cyano or nitro, $R^2$ represents hydrogen, or represents in each case unsubstituted or fluorine- and/or chlorine-substituted $C_1$–$C_4$-alkyl, $C_3$–$C_4$-alkenyl, $C_3$–$C_4$-alkinyl, $C_1$–$C_4$-alkoxy, $C_3$–$C_4$-alkenyloxy or represents phenyl, benzyl or benzyloxy, each of which is unsubstituted or mono- to disubstituted by fluorine, chlorine, bromine, $C_1$–$C_4$-alkyl, $C_1$–$C_4$-alkoxy, $C_1$–$C_2$-halogeno-alkyl, $C_1$–$C_2$-halogenoalkoxy, cyano or nitro, or $R^1$, $R^2$ together with the nitrogen atom to which they are attached represent an unsubstituted or $C_1$–$C_2$-alkyl-substituted five- or six-membered cycle wherein optionally one methylene group may be replaced by oxygen, $R^3$ represents hydrogen, or represents $C_1$–$C_4$-alkyl or represents phenyl or benzyl, each of which is unsubstituted or mono- to disubstituted by fluorine, chlorine, bromine, $C_1$–$C_4$-alkyl, $C_1$–$C_4$-alkoxy, trifluoromethyl, difluoromethoxy, trifluoromethoxy, cyano or nitro, $R^4$, $R^5$, $R^6$ each represents hydrogen, methyl or ethyl, $R^7$ represents in each case unsubstituted or fluorine- and/or chlorine-substituted $C_1$–$C_6$-alkyl, $C_2$–$C_6$-alkenyl, $C_3$–$C_6$-alkinyl, $C_1$–$C_6$-alkoxy, $C_1$–$C_4$-alkoxy-$C_1$–$C_2$-alkyl, $C_1$–$C_4$-alkylthio-$C_1$–$C_2$-alkyl, or represents in each case unsubstituted or fluorine- and/or chlorine-, $C_1$–$C_2$-alkyl, $C_1$–$C_2$-alkoxy-substituted $C_3$–$C_6$-cycloalkyl wherein optionally one methylene group may be replaced by oxygen, or represents phenyl, phenoxy, benzyloxy, thienyl, furanyl, pyridyl, pyrimidyl, thiazolyl, pyrazolyl or phenyl-$C_1$–$C_2$-alkyl, each of which is unsubstituted or mono- to disubstituted by fluorine, chlorine, bromine, $C_1$–$C_4$-alkyl, $C_1$–$C_4$-alkoxy, trifluoromethyl, difluoromethoxy, trifluoromethoxy, cyano or nitro, or, in the case of the radicals a) and c) mentioned under Ar, also represents a group

or, for the radical g), also represents hydroxyl, $R^8$ represents hydrogen, $R^9$ represents hydrogen, or represents unsubstituted or fluorine- and/or chlorine-substituted $C_1$–$C_6$-alkyl, $C_3$–$C_6$-alkenyl, $C_3$–$C_6$-alkinyl, $C_1$–$C_6$-alkoxy, $C_3$–$C_6$-cycloalkyl, wherein optionally one methylene group may be replaced by oxygen, or represents phenyl or phenyl-$C_1$–$C_2$-alkyl, each of which is unsubstituted or mono- to disubstituted by fluorine, chlorine, bromine, $C_1$–$C_4$-alkyl, $C_1$–$C_4$-alkoxy, trifluoromethyl, difluoromethoxy, trifluoromethoxy, cyano or nitro, $R^{10}$ represents hydrogen or $C_1$–$C_4$-alkyl, or $R^9$, $R^{10}$ together with the nitrogen atom to which they are attached represent an unsubstituted or $C_1$–$C_2$-alkyl-substituted five- to six-membered cycle wherein optionally one methylene group may be replaced by oxygen, and m represents 0 to 1, and
n depending on m, represents 0 to 2.

3. A compound according to claim 1, wherein
K represents oxygen or sulphur,
Ar represents $Ar^1$, where $Ar^1$ is selected from the group consisting of
  i) phenyl being substituted with from one to three substituents, and
  ii) thienyl, pyrimidyl, furanyl or pyridyl, each of which is substituted with zero to three substituents,
  with said substituents being selected from the group consisting of fluorine, chlorine, bromine, methyl, ethyl, propyl, i-propyl, s-, n-, i- or t-butyl, methoxy, ethoxy, propoxy, i-propoxy, s-, n-, i- or t-butoxy, allyloxy, methallyloxy, 2-butenyloxy, propargyloxy, 2-butinyloxy, methylthio, ethylthio, methylsulfinyl, ethylsulfinyl, methylsulfonyl, ethylsulfonyl, trifluoromethyl, difluoromethoxy, trifluoromethoxy, methylenedioxy, difluoromethylenedioxy, tetrafluoroethylenedioxy, difluoromethylthio, trifluoromethylthio, trifluoromethylsulfinyl, trifluoromethylsulfonyl, hydroxyl, mercapto, nitro, cyano, amino,

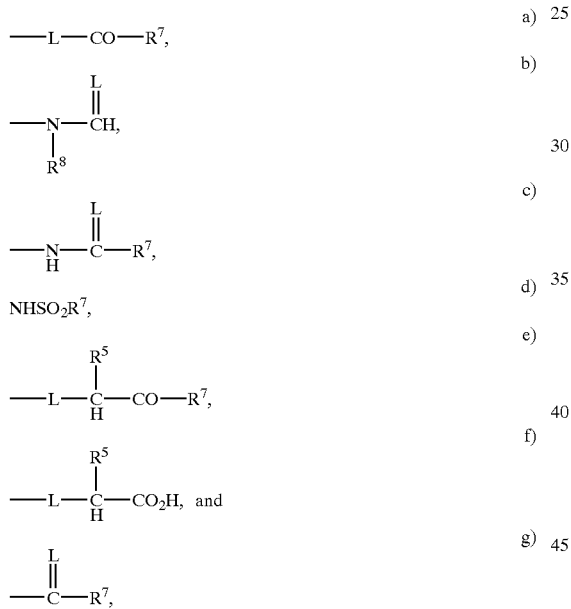

or Ar represents $Ar^2$, where $Ar^2$ represents $Ar^1$ which is additionally substituted by phenyl, pyridyl, thienyl, tetrazolyl, triazolyl or phenoxy, where these substituents for their part are unsubstituted or mono- to disubstituted by fluorine, chlorine, bromine, methyl, ethyl, n- or i-propyl, s-, n-, i- or t-butyl, methoxy, ethoxy, i-propoxy, s-, n- or t-butoxy, trifluoromethyl, trifluoromethoxy, nitro or cyano, and
L represents oxygen or sulphur,
X represents

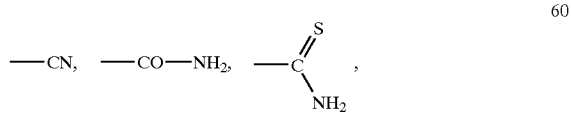

Y represents methyl, phenyl which is unsubstituted or mono- to tri-substituted by fluorine, chlorine, bromine, methyl, methoxy, trifluoromethyl or trifluoromethoxy, or represents the group $—CO_2R^1$, or two adjacent $Y_n$ represent a six-membered unsaturated cycle, which may be unsubstituted or monosubstituted by fluorine, chlorine, bromine, methyl, methoxy, trifluoromethyl, trifluoromethoxy, cyano or nitro, and Z represents hydrogen, methyl, ethyl, allyl, propargyl, cyclopropyl, cyclopentyl, cyclohexyl, cyclopropylmethyl, cyclopentylmethyl, cyclohexylmethyl, methoxymethyl, ethoxymethyl, or represents phenyl, benzyl, pyridylmethyl, thiazolylmethyl, each of which is unsubstituted or mono- to disubstituted by fluorine, chlorine, bromine, methyl, methoxy, trifluoromethyl or trifluoromethoxy, cyano or nitro, or represents the groups

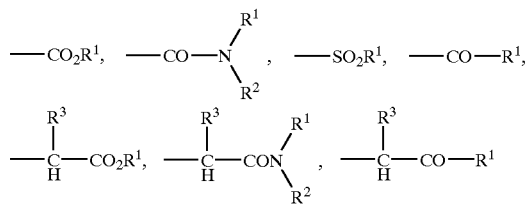

or cyano,
$R^1$ represents hydrogen (but not for the radicals $—CO_2R^1$ and $—SO_2R^1$), methyl, ethyl, propyl, isopropyl, n-, s-, i- or t-butyl, allyl, propargyl, cyclopropyl, cyclopentyl, cyclohexyl, or represents phenyl or benzyl, each of which is unsubstituted or mono- to disubstituted by fluorine, chlorine, bromine, methyl, methoxy, trifluoromethyl, trifluoromethoxy, cyano or nitro,
$R^2$ represents hydrogen, methyl, ethyl, propyl, isopropyl, allyl, propargyl, methoxy, ethoxy, allyloxy or represents benzyloxy which is unsubstituted or mono- to disubstituted by fluorine, chlorine, bromine, methyl, methoxy, trifluoromethyl, trifluoromethoxy, cyano or nitro, or
$R^1$, $R^2$ together with the nitrogen atom to which they are attached represent a pyrrolidone, piperidine, thiazine or morpholine radical,
$R^3$, $R^5$ each represent hydrogen, methyl or ethyl,
$R^7$ represents methyl, ethyl, propyl, isopropyl, n-, s-, i- or t-butyl, vinyl, trifluoromethyl, methoxy, ethoxy, propoxy, isopropoxy, n-, s-, i- or t-butyloxy, cyclopropyl, cyclopentyl, cyclohexyl, cyclopentyloxy, cyclohexyloxy, or represents phenyl, pyridyl or benzyl, each of which is unsubstituted or mono- to disubstituted by fluorine, chlorine, bromine, methyl, n-, s-, i- or t-butyl, methoxy, trifluoromethyl, trifluoromethoxy, cyano or nitro, or, in the case of the radicals a) and c) mentioned under Ar, also represents a group

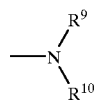

or, for the radical g), also represents hydroxyl,
$R^9$ represents hydrogen, methyl, ethyl, propyl, isopropyl, n-, s-, i- or t-butyl, cyclopropyl, cyclopentyl, cyclohexyl, or represents phenyl which is unsubstituted or mono- to disubstituted by fluorine, chlorine, bromine, methyl, methoxy, trifluoromethyl, trifluoromethoxy, cyano or nitro, $R^{10}$ represents hydrogen, methyl or ethyl, or $R^9$, $R^{10}$ together with the nitrogen atom to which they are attached represent a pyrrolidine, piperidine or morpholine radical, and m represents 1 to 3, and n depending on m, represents 0 to 1.

4. A compound according to claim 1, wherein

K represents oxygen or sulphur,

Ar represents $Ar^1$, where $Ar^1$ is selected from the group consisting of
- i) phenyl being substituted with from one to three substituents, and
- ii) thienyl, pyrimidyl or pyridyl, having zero to three substituents, with said substituents being selected from the group consisting of fluorine, chlorine, bromine, methyl, ethyl, propyl, isopropyl, n-, s-, i- or t-butyl, methoxy, ethoxy, propoxy, isopropoxy, tert-butoxy, allyloxy, methallyloxy, 2-butenyloxy, propargyloxy, 2-butinyloxy, methylthio, ethylthio, methylsulphinyl, ethylsulphinyl, methylsulphonyl, ethylsulphonyl, trifluoromethyl, difluoromethoxy, trifluoromethoxy, methylenedioxy, difluoromethylenedioxy, tetrafluoroethylenedioxy, difluoromethylthio, trifluoromethylthio, triflouromethylsulphinyl, trifluoromethylsulphonyl, hydroxyl, mercapto, nitro, cyano, and amino, or Ar represents $Ar^2$, where $Ar^2$ represents $Ar^1$ which is additionally substituted by phenyl or phenoxy, where these substituents are unsubstituted or mono- to disubstituted by fluorine, chlorine, bromine, methyl, ethyl, isopropyl, n-, s-, i- or t-butyl, methoxy, ethoxy, isopropoxy, n-, s-, i- or t-butoxy, trifluoromethyl, trifluoromethoxy, nitro or cyano, X represents CN, Z represents hydrogen or methyl, m represents 1 to 3, and n represents 0.

5. A process for preparing a compound according to claim 1, comprising the step of (A) in the case where K represents oxygen and Z represents hydrogen, reacting a compound of the formula (II)

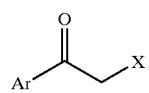

(II)

wherein

Ar and X are each as defined in claim 13, with a compound of the formula (III)

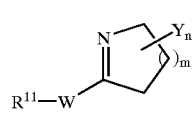

(III)

wherein

Y, m, n are each as defined in claim 13, and

W represents O or $S(O)_g$, where g represents 0 or 2, and $R^{11}$ represents alkyl or benzyl, or (B) in the case where K represents oxygen and Z represents hydrogen, reacting a compound of the formula (IV)

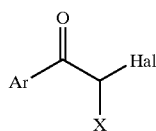

(IV)

wherein

Ar and X are each as defined in claim 13 and

Hal represents halogen, with a compound of the formula (V)

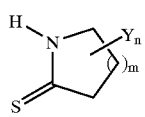

(V)

wherein

Y, m and n are each as defined in claim 13, to give a compound of the formula (VI)

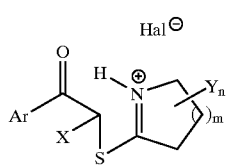

(VI)

wherein

Ar, X, Y, m and n are each as defined in claim 13, reacting the compound of the formula (VI) with elimination of sulphur and hydrogen halide, to give a compound of the formula (I)

wherein

Ar, X, Y, m and n are each as defined in claim 13 and

Z represents hydrogen, or (C) in the case where K represents oxygen and Z does not represent hydrogen reacting a compound of the formula (VII)

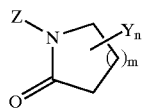

(VII)

wherein

Y, m and n are each as defined in claim 13 with a halogenating agent to give a compound of the formula (VIII)

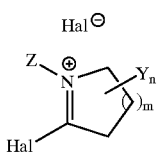

(VIII)

wherein
Y, Z, m and n are each as defined in claim 13 and Z does not represent hydrogen, and
Hal represents halogen,
reacting the compound of the formula (VIII) with a compound of the formula (II)

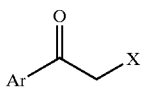

(II)

wherein
Ar, X are each as defined in claim 13
or
(D) in the case where K represents oxygen and Z does not represent hydrogen, reacting a compound of the formula (I-a)

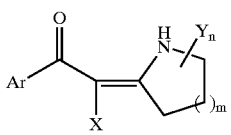

(I-a)

wherein
Ar, X, Y, m and n are each as defined in claim 13 with an agent selected from alkylating agents, acylating agents, sulphonylating agents and condensing agents of the formula (IX)

Z—G       (IX), wherein
G represents halogen, sulphonate or alkoxy, or
(E) in the case where Ar represents $Ar^2$ according to claim 1, reacting a compound of the formula ($I^1$)

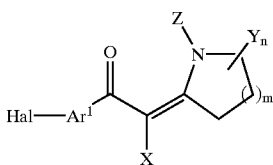

($I^1$)

wherein
$Ar^1$, X, Y, Z, m and n are each as defined in claim 13 and
Hal represents halogen, with a boronic acid of the formula (X)

$Ar^{2'}$—B(OH)$_2$       (X), wherein
$Ar^2$ represents $Ar^1$ which is additionally substituted by phenyl, naphthyl, five- or six-membered hetaryl, phenyl-$C_1$–$C_4$-alkyl, phenoxy, phenyl-S(O)$_g$—, five- or six-membered hetaryloxy or hetaryl-S(O)$_g$, where these substituents for their part are in each case unsubstituted or mono- to tetrasubstituted by halogen, $C_1$–$C_6$-alkyl, $C_1$–$C_6$-alkoxy, $C_1$–$C_4$-halogenoalkyl, $C_1$–$C_4$-halo-genoalkoxy, nitro or cyano,
$Ar^{2'}$ represents the substituents which were mentioned in claim 13 as additional substituents for $Ar^1$, in the presence of a solvent, or
(F) reacting a compound of the formula (I)

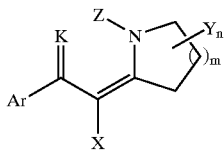

(I)

wherein
Ar, X, Y, Z, m and n are each as defined in claim 13,
and K represents oxygen,
with a sulphurizing agent in the presence of a solvent.

6. A herbicidal composition comprising a compound according to claim 1 and an extender selected from the group consisting of liquid solvents, solid carriers and mixtures thereof.

7. An acaricidal composition comprising a compound according to claim 1 and an extender selected from the group consisting of liquid solvents, solid carriers ard mixtures thereof.

8. An insecticide composition comprising a compound according to claim 1 and an extender selected from the group consisting of liquid solvents, solid carriers and mixtures thereof.

9. A method of controlling undesirable vegetation comprising the steps of applying a compound according to claim 1 to said vegetation.

10. A method of controlling animal pests comprising the step of applying a compound according to claim 1 to said pests or their habitats.

11. A method according to claim 10, wherein the animal pests are selected from arthropods and nematodes.

* * * * *